(12) United States Patent
Luche et al.

(10) Patent No.: US 6,902,919 B2
(45) Date of Patent: Jun. 7, 2005

(54) DSP-12 AND DSP-13 DUAL-SPECIFICITY PHOSPHATASES

(75) Inventors: Ralf M. Luche, Seattle, WA (US); Bo Wei, Kirkland, WA (US)

(73) Assignee: CEPTYR, Inc., Bothell, WA (US)

( * ) Notice: Subject to any disclaimer, the term of this patent is extended or adjusted under 35 U.S.C. 154(b) by 373 days.

(21) Appl. No.: 09/775,925

(22) Filed: Feb. 1, 2001

(65) Prior Publication Data

US 2001/0049358 A1 Dec. 6, 2001

Related U.S. Application Data

(60) Provisional application No. 60/179,886, filed on Feb. 2, 2000.

(51) Int. Cl.$^7$ ............................ C12N 9/12; C12N 1/20; C12N 15/00; C07H 21/04; C07K 1/00
(52) U.S. Cl. ................. 435/194; 435/252.3; 435/320.1; 536/23.2; 530/350
(58) Field of Search .............................. 435/194, 252.3, 435/320.1, 69.1; 536/23.2, 23.1; 530/350

(56) References Cited

FOREIGN PATENT DOCUMENTS

| WO | WO 97/00315 | 1/1997 |
|---|---|---|
| WO | WO 97/06245 | 2/1997 |
| WO | WO 98/04712 | 2/1998 |
| WO | WO 01/46394 | 6/2001 |
| WO | WO 01/53469 | 7/2001 |

OTHER PUBLICATIONS

Adams and Cory, "The Bcl–2 Protein Family: Arbiters of Cell Survival," *Science* 281(5381):1322–1326, Aug. 28, 1998.
Alessi et al., "The Human CL100 Gene Encodes a Tyr/Thr – Protein Phosphatase Which Potently and Specifically Inactivates MAP Kinase and Suppresses Its Activation by Oncogenic Ras in Xenopus Oocyte Extracts," *Oncogene* 8(7):2015–2020, Jul. 1993.
Ashkenazi and Dixit, "Death Receptors: Signaling and Modulation," *Science* 281(5381). 1305–1308, Aug. 28, 1998.
Evan and Littlewood, "A Matter of Life and Cell Death," *Science* 281(5381):1317–1322, Aug. 28, 1998.
Fauman and Saper, "Structure and Function of the Protein Tyrosine Phosphatases," *TiBS* 21(11):413–417, Nov. 1996.
Frohman et al., "Rapid Production of Full–Length cDNAs from Rare Transcripts: Amplification using a Single Gene–Specific Oligonucleotide Primer," *PNAS* 85(23):8998–9002, Dec. 1988.
GenBank Acc. No. AC004099, Jun. 6, 2000.
Groom et al., "Differential Regulation of the MAP, SAP and RK p38 Kinases by Pyst 1, a Novel Cytosolic Dual–Specificity Phosphatase," *The EMBO J* 15(14):3621–3632, Jul. 15, 1996.

Guan and Butch, "Isolation and Characterization of a Novel Dual Specific Phosphatase, HVH2, Which Selectively Dephosphorylates the Mitogen–Activated Protein Kinase," *The J. of Biological Chemistry* 270(13):7197–7203, Mar. 31, 1995.
Jia, "Protein Phosphatases: Structures and Implications," *Biochem. Cell. Biol.* 75(1):17–26.
Keyse and Emslie, "Oxidative Stress and Heat Shock Induce a Human Gene Encoding a Protein–Tyrosine Phosphatase," *Nature* 359:644–647, Oct. 15, 1992.
Loh et al., "Polymerase Chain Reaction with Single–Sided Specificity: Analysis of T Cell Receptor δ Chain," *Science* 243(4888):217–220, Jan. 13, 1989.
Ohara et al., "One–Sided Polymerase Chain Reaction: the Amplification of cDNA," *PNAS* 86(15):5673–5677, Aug. 1989.
Thornberry and Lazebnik, "Caspases: Enemies Within," *Science* 281(5381):1312–1316, Aug. 28, 1998.
Walton and Dixon, "Protein Tyrosine Phosphatases," *Annu. Rev. Biochem.* 62:101–120, 1993.
Ward et al., "Control of MAP Kinase Activation by the Mitogen–Induced Threonine Tyrosine Phosphatase PAC1," *Nature* 367(6464):651–654, Feb. 17, 1994.
Zheng and Guan, "Dephosphorylation and Inactivation of the Mitogen–Activated Protein Kinase by a Mitogen–Induced Thr/Tyr Protein Phosphatase" *The Journal of Biological Chemistry*, 368(22):16116–16119, Aug. 5, 1993.
Flint et al., "Development of 'Substrate–Trapping' Mutations to Identify Physiological Substrates of Protein Tyrosine Phosphatases," *P.N.A.S. USA* 94:1680–1685, Mar. 1, 1997.
Keyse, "An Emerging Family of Dual Specificity MAP Kinase Phosphatases," *Biochimica et Biophisica Acta* 1265:152–160, 1995.
Muda et al., "Molecular Cloning and Functional Characterization of a Novel Mitogen– Activated Protein Kinase Phosphatase, MKP–4," *J. Biological Chemistry* 272(8):5141–5151, 1997.
GenBank database, Accession No. AB036834, Apr. 3, 2001.
GenBank database, Accession No. AC008081, Nov. 24, 2000.
GenBank database, Accession No. AC010189, Jan. 7, 2001.

*Primary Examiner*—Tekchand Saidha
(74) *Attorney, Agent, or Firm*—SEED Intellectual Property Law Group PLLC

(57) ABSTRACT

Compositions and methods are provided for the treatment of conditions associated with cell proliferation, cell differentiation and cell survival. In particular, the dual-specificity phosphatases DSP-12 and DSP-13, and polypeptide variants thereof that stimulate dephosphorylation of DSP-12 and DSP-13 substrates, are provided. The polypeptides may be used, for example, to identify antibodies and other agents that inhibit DSP-12 and/or DSP-13 activity. The polypeptides and agents may be used to modulate cell proliferation, differentiation and survival.

13 Claims, 7 Drawing Sheets

Figure 1

DSP-12, 1656 Base Pairs

```
AAGCAGTGGTAACAACGCAGAGTACGCGGGCGAGGAGAATATCTTGCTGGGAGTGGACT
TTTCCAGTAAGGAAAGTAAAAGCTGCACCATTGGGATGGTTCTCCGACTGTGGAGCGAC
ACGAAAATCCACCTTGATGGAGATGGTGGGTTCAGCGTGAGCACAGCAGGAAGGATGCA
CATATTTAAGCCTGTGTCTGTCCAGGCCATGTGGTCTGCCCTGCAGGTGCTTCACAAGG
CCTGCGAAGTGGCCCGGAGGCACAACTACTTCCCCGGGGGTGTAGCTCTCATCTGGGCT
ACCTACTATGAGAGCTGCATCAGCTCCGAGCAGAGCTGCATCAACGAGTGGAACGCCAT
GCAGGACCTGGAGTCTACGCGGCCCGACTCCCCCGCGCTATTTGTGGACAAGCCCACTG
AAGGGGAAAGGACCGAGCGCCTCATCAAAGCCAAGCTCCGAAGCATCATGATGAGCCAG
GATCTAGAAAATGTGACTTCCAAAGAGATTCGTAATGAATTAGAGAAACAGATGAATTG
TAACTTGAAGGAACTCAAGGAATTTATAGACAATGAGATGCTACTTATCTTGGGACAGA
TGGACAAGCCCTCCCTTATCTTCGATCATCTTTATCTCGGCTCTGAATGGAATGCATCC
AATCTGGAGGAACTGCAGGGCTCAGGGGTTGATTACATTTTAAATGTTACCAGAGAAAT
CGATAATTTTTTTCCTGGCTTATTTGCATATCATAACATCCGAGTCTACGATGAAGAGA
CCACAGACCTCCTCGCCCACTGGAATGAAGCGTATCATTTTATAAACAAAGCGAAGAGG
AACCATTCCAAGTGCCTGGTGCATTGCAAAATGGGCGTGAGTCGCTCGGCCTCCACAGT
CATAGCCTATGCAATGAAGGAATTCGGCTGGCCTCTGGAAAAAGCATATAACTATGTAA
AGCAGAAGCGCAGCATCACGCGCCCCAACGCGGGCTTTATGAGGCAGCTGTCTGAGTAT
GAAGGCATCTTGGATGCAAGCAAACAGCGGCACAACAAGCTGTGGCGTCAGCAGACAGA
CAGCAGCCTCCAGCAGCCTGTGGATGACCCTGCAGGACCTGGCGACTTCTTGCCAGAGA
CCCCAGATGGCACCCCGGAAAGCCAGCTGCCCTTCTTGGATGATGCCGCCCAGCCCGGC
TTAGGGCCCCCCCTCCCCTGCTGTTTCCGGCGACTCTCAGACCCCCTTCTGCCTTCCCC
TGAGGATGAAGCCGGCAGCTTGGTCCACCTGGAGGATCCGGAGAGGGAGGCTCTGTTGG
AGGAAGCTGCTCCACCTGCAGAGGTGCACAGGCCGGCCAGACAGCCCCAGCAAGGTTCC
GGACTCTGTGAGAAGGATGTGAAGAAGAAACTAGAGTTTGGGAGTCCCAAAGGTCGGAG
CGGCTCCTTGCTGCAGGTGGAGGAGACGGAAAGGGAGGAGGGCCTGGGAGCAGGGAGGT
GGGGGCAGCTTCCAACCCAGCTCGATCAAAACCTGCTCAACTCGGAGAACCTAAACAAC
AACAGCAAGAGGAGCTGTCCCAACGGCATGGAGGTAGGCAGAGCCCGGCCTGCAGGGTG
GCACACCCCATCCCTTCCATCCCACTCTAATTGGCCTACCTCAGCCTCTGTAGTAGGGA
CTACAGGCACCCGCCACCACACCCAGCTGATTTTTTCTATTGTCTCCTCTGGGCCCCC
AGCTCCCATCTCCAGGGACCTGAGGGTTCTTTCACAGGGTGATTCTGCTGGTGGGTACG
TAGTGCATACCTTATATAGCAAATTGAGAATCTGTTGGGAATAACACATATCTCTGCAC
ACCATCTTCACCCCATGTACCTTATTCATACCCTGGGCAGGGCTTCCAACTCAATTTCT
TTTTGTGTATGTAAAATTAAAACATATAATTTATCAGCCAAAAAAAAAAAAAAAAAAAA
AA
```

Figure 2

DSP-12, 552 Amino Acids

MVLRLWSDTKIHLDGDGGFSVSTAGRMHIFKPVSVQAMWSALQVLHKACEVARRHNYFP
GGVALIWATYYESCISSEQSCINEWNAMQDLESTRPDSPALFVDKPTEGERTERLIKAK
LRSIMMSQDLENVTSKEIRNELEKQMNCNLKELKEFIDNEMLLILGQMDKPSLIFDHLY
LGSEWNASNLEELQGSGVDYILNVTREIDNFFPGLFAYHNIRVYDEETTDLLAHWNEAY
HFINKAKRNHSKCLVHCKMGVSRSASTVIAYAMKEFGWPLEKAYNYVKQKRSITRPNAG
FMRQLSEYEGILDASKQRHNKLWRQQTDSSLQQPVDDPAGPGDFLPETPDGTPESQLPF
LDDAAQPGLGPPLPCCFRRLSDPLLPSPEDEAGSLVHLEDPEREALLEEAAPPAEVHRP
ARQPQQGSGLCEKDVKKKLEFGSPKGRSGSLLQVEETEREEGLGAGRWGQLPTQLDQNL
LNSENLNNNSKRSCPNGMEVGRARPAGWHTPSLPSHSNWPTSASVVGTTGTRHHTQLIF
FYCLLWAPSSHLQGPEGSFTG

Figure 3

DSP-13, 1527 Base Pairs

```
CCTGGGAAGAAGTTATCTATCTCTCGAGTGACATTCAAGATATACCGTACCCCTCGGTTCTGTA
AGTCCTCTAAGTTGGAGGCATTCCATTCTGAGCCGGCCCCATGACCCTGAGCACGTTGGCCCGC
AAGAGGAAGGCGCCCCTCGCTTGCACCTGCAGCCTCGGTGGCCCCGACATGATTCCTTACTTCT
CCGCCAACGCGGTCATCTCGCAGAACGCCATCAACCAGCTCATCAGCGAGAGCTTTCTAACTGT
CAAAGGTGCTGCCCTTTTTCTACCACGGGGAAATGGCTCATCCACACCAAGAATCAGCCACAGA
CGGAACAAGCATGCAGGCGATCTCCAACAGCATCTCCAAGCAATGTTCATTTTACTCCGCCCAG
AAGACAACATCAGGCTGGCTGTAAGACTGGAAAGTACTTACCAGAATCGAACACGCTATATGGT
AGTGGTTTCAACTAATGGTAGACAAGACACTGAAGAAAGCATCGTCCTAGGAATGGATTTCTCC
TCTAATGACAGTAGCACTTGTACCATGGGCTTAGTTTTGCCTCTCTGGAGCGACACGCTAATTC
ATTTGGATGGTGATGGTGGGTTCAGTGTATCGACGGATAACAGAGTTCACATATTCAAACCTGT
ATCTGTGCAGGCAATGTGGTCTGCACTACAGAGCTTACACAAGGCTTGTGAAGTCGCCAGAGCG
CATAACTACTACCCAGGCAGCCTATTTCTCACTTGGGTGAGTTATTATGAGAGCCATATCAACT
CAGATCAATCCTCAGTCAATGAATGGAATGCAATGCAAGATGTACAGTCCCACCGGCCCGACTC
TCCAGCTCTCTTCACCGACATACCTACTGAACGTGAACGAACAGAAAGGCTAATTAAAACCAAA
TTAAGGGAGATCATGATGCAGAAGGATTTGGAGAATATTACATCCAAAGAGATAAGAACAGAGT
TGGAAATGCAAATGGTGTGCAACTTGCGGGAATTCAAGGAATTTATAGACAATGAAATGATAGT
GATCCTTGGTCAAATGGATAGCCCTACACAGATATTTGAGCATGTGTTCCTGGGCTCAGAATGG
AATGCCTCCAACTTAGAGGACTTACAGAACCGAGGGGTACGGTATATCTTGAATGTCACTCGAG
AGATAGATAACTTCTTCCCAGGAGTCTTTGAGTATCATAACATTCGGGTATATGATGAAGAGGC
AACGGATCTCCTGGCGTACTGGAATGACACTTACAAATTCATCTCTAAAGCAAAGAAACATGGA
TCTAAATGCCTTGTGCACTGCAAAATGGGGGTGAGTCGCTCAGCCTCCACCGTGATTGCCTATG
CAATGAAGGAATATGGCTGGAATCTGGACCGAGCCTATGACTATGTGAAAGAAAGACGAACGGT
AACCAAGCCCAACCCAAGCTTCATGAGACAACTGGAAGAGTATCAGGGGATCTTGCTGGCAAGC
TTCCTAGGCTTGATTCATGGAGGGAGGGACAAGCCCTGGGGAGAGAAAAGCACAGAATTTGAGT
CAGTAGATCTGGTTTCCATTCCTGGTTCACCCTCTTGCTGCAACCCTGAGAAGTTACTTCACAT
TTCTCATCCTTACCTGACCCCATCTATAAAATGAAAATCAAGAGATCCATCTCACAGGGTTATT
GTGAATAAAAATGTGTTTGAATGTTTATAAAAAAAAAAAAAAAAAA
```

Figure 4

DSP-13, 509 Amino Acids

MTLSTLARKRKAPLACTCSLGGPDMIPYFSANAVISQNAINQLISESFLTVKGAALFLPRGNGS
STPRISHRRNKHAGDLQQHLQAMFILLRPEDNIRLAVRLESTYQNRTRYMVVVSTNGRQDTEES
IVLGMDFSSNDSSTCTMGLVLPLWSDTLIHLDGDGGFSVSTDNRVHIFKPVSVQAMWSALQSLH
KACEVARAHNYYPGSLFLTWVSYYESHINSDQSSVNEWNAMQDVQSHRPDSPALFTDIPTERER
TERLIKTKLREIMMQKDLENITSKEIRTELEMQMVCNLREFKEFIDNEMIVILGQMDSPTQIFE
HVFLGSEWNASNLEDLQNRGVRYILNVTREIDNFFPGVFEYHNIRVYDEEATDLLAYWNDTYKF
ISKAKKHGSKCLVHCKMGVSRSASTVIAYAMKEYGWNLDRAYDYVKERRTVTKPNPSFMRQLEE
YQGILLASFLGLIHGGRDKPWGEKSTEFESVDLVSIPGSPSCCNPEKLLHISHPYLTPSIK

Figure 5

A    DSP13 Alternate Splice Variant, 723 Base Pairs

CTGCCCGGCTTCTAACAGGCCACTGACCGGTACTCACTGGGGACCCACGCTCTAAGTTGTTGAT
CTCTAGAACCGATTTTGGAAAAGGATTTGCCTTATTGAAGAAGACAGGATCATTCTTCTTTCTT
TCCCATTTAAGAATAATCGTTATTAAGAATATCGTTTAAGAATAATCGTTATTTCTCTCTTCTC
AGACCTACTGAACGTGAACGAACAGAAAGGCTAATTAAAACCAAATTAAGGGAGATCATGATGC
AGAAGGATTTGGAGAATATTACATCCAAAGAGATAAGAACAGAGTTGGAAATGCAAATGGTGTG
CAACTTGCGGGAATTCAAGGAATTTATAGACAATGAAATGATAGTGATCCTTGGTCAAATGGAT
AGCCCTACACAGATATTTGAGCATGTGTTCCTGGGCTCAGAATGGAATGCCTCCAACTTAGAGG
ACTTACAGAACCGAGGGGTACGGTATATCTTGAATGTCACTCGAGAGATAGATAACTTCTTCCC
AGGAGTCTTTGAGTATCATAACATTCGGGTATATGATGAAGAGGCAACGGATCTCCTGGCGTAC
TGGAATGACACTTACAAATTCATCTCTAAAGCAAAGAAACATGGATCTAAATGCCTTGTGCACT
GCAAAATGGGGGTGAGTCGCTCAGCCTCCACCGTGATTGCCTATGCAATGAAGGAATATGGCTG
GAATCTGGACCGAGCCTATGACTATGTGAAAGAAAGACGAACGGTAACCAAGCCCAACCCAAGC
TTCATGAGACAACTGGAAGAGTATCAGGGGATCTTGCTGGCAAGCTTCCTAGGCTTGATTCATG
GAGGGAGGGACAAGCCCTGGGGAGAGAAAAGCACAGAATTTGAGTCAGTAGATCTGGTTTCCAT
TCCTGGTTCACCCTCTTGCTGCAACCCTGAGAAGTTACTTCACATTTCTCATCCTTACCTGACC
CCATCTATAAAATGAAAATCAAGAGATCCATCTCACAGGGTTATTGTGAATAAAAATGTGTTTG
AATGTTTATAAAAAAAAAAAAAAAAAAA

B    DSP13 Alternate Splice Variant, 241 Amino Acids

MMQKDLENITSKEIRTELEMQMVCNLREFKEFIDNEMIVILGQMDSPTQIFEHVFLGSEWNASN
LEDLQNRGVRYILNVTREIDNFFPGVFEYHNIRVYDEEATDLLAYWNDTYKFISKAKKHGSKCL
VHCKMGVSRSASTVIAYAMKEYGWNLDRAYDYVKERRTVTKPNPSFMRQLEEYQGILLASFLGL
IHGGRDKPWGEKSTEFESVDLVSIPGSPSCCNPEKLLHISHPYLTPSIK

DSP-12 AND DSP-13 DUAL-SPECIFICITY PHOSPHATASES

CROSS-REFERENCE TO RELATED APPLICATION

This application claims the benefit of U.S. Ser. No. 60/179,886, filed Feb. 2, 2000, which is incorporated herein by reference in its entirety.

The present invention relates generally to compositions and methods useful for treating conditions associated with defects in cell proliferation, cell differentiation and/or cell survival. The invention is more particularly related to dual-specificity protein phosphatases, and polypeptide variants thereof. The present invention is also related to the use of such polypeptides to identify antibodies and other agents, including small molecules, that modulate signal transduction leading to proliferative responses, cell differentiation and/or cell survival.

BACKGROUND OF THE INVENTION

Mitogen-activated protein kinases (MAP-kinases) are present as components of conserved cellular signal transduction pathways that have a variety of conserved members. MAP-kinases are activated by phosphorylation at a dual phosphorylation motif with the sequence Thr-X-Tyr (by MAP-kinase kinases), in which phosphorylation at the tyrosine and threonine residues is required for activity. Activated MAP-kinases phosphorylate several transduction targets including transcription factors. Inactivation of MAP-kinases is mediated by dephosphorylation at this site by dual-specificity phosphatases referred to as MAP-kinase phosphatases. In higher eukaryotes, the physiological role of MAP-kinase signaling has been correlated with cellular events such as proliferation, oncogenesis, development and differentiation. Accordingly, the ability to regulate signal transduction via these pathways could lead to the development of treatments and preventive therapies for human diseases associated with MAP-kinase signaling, such as cancer.

Dual-specificity protein tyrosine phosphatases (dual-specificity phosphatases) are phosphatases that dephosphorylate both phosphotyrosine and phosphothreonine/serine residues (Walton et al., *Ann. Rev. Biochem.* 62:101–120, 1993). Several dual-specificity phosphatases that inactivate a MAP-kinase have been identified, including MKP-1 (WO 97/00315; Keyse and Emslie, *Nature* 59:644–647, 1992), MKP-4, MKP-5, MKP-7, Hb5 (WO 97/06245), PAC1 (Ward et al., *Nature* 367:651–654, 1994), HVH2 (Guan and Butch, *J. Biol. Chem.* 270:7197–7203, 1995), PYST1 (Groom et al., *EMBO J.* 15:3621–3632, 1996) and others (see, e.g., WO 95/21923). Expression of certain dual-specificity phosphatases is induced by stress or mitogens, but others appear to be expressed constitutively in specific cell types. The regulation of dual-specificity phosphatase expression and activity is critical for control of MAP-kinase mediated cellular functions including cell proliferation, cell differentiation and cell survival. For example, dual-specificity phosphatases may function as negative regulators of cell proliferation. It is likely that there are many such dual-specificity phosphatases, with varying specificity with regard to cell type or activation. However, the regulation of dual specificity phosphatases remains poorly understood and only a relatively small number of dual-specificity phosphatases have been identified.

Accordingly, there is a need in the art for an improved understanding of MAP-kinase signaling, and the regulation of dual-specificity phosphatases within MAP-kinase signaling cascades. An increased understanding of dual-specificity phosphatase regulation may facilitate the development of methods for modulating the activity of proteins involved in MAP-kinase cascades, and for treating conditions associated with such cascades. The present invention fulfills these needs and further provides other related advantages.

SUMMARY OF THE INVENTION

Briefly stated, the present invention provides compositions and methods for identifying agents capable of modulating cellular proliferative responses. In one aspect, the present invention provides isolated DSP-12 polypeptides having the sequence of DSP-12 recited in SEQ ID NO:2, or a variant thereof that differs in one or more amino acid deletions, additions, insertions or substitutions at no more than 50% of the residues in SEQ ID NO:2, such that the polypeptide retains the ability to dephosphorylate an activated MAP-kinase.

Within further aspects, the present invention provides an isolated polynucleotide that encodes at least ten consecutive amino acids of a polypeptide having a sequence corresponding to SEQ ID NO:2. In certain embodiments the invention provides an isolated polynucleotide that encodes at least fifteen consecutive amino acids of a polypeptide having a sequence corresponding to SEQ ID NO:2. Certain such polynucleotides encode a DSP-12 polypeptide. Still further, polynucleotides may be antisense polynucleotides that comprise at least 15 consecutive nucleotides complementary to a portion of a DSP-12 polynucleotide and/or that detectably hybridize to the complement of the sequence recited in SEQ ID NO:1 under conditions that include a wash in 0.1×SSC and 0.1% SDS at 60° C. for 15 minutes. Also provided are expression vectors comprising any of the foregoing polynucleotides, and host cells transformed or transfected with such expression vectors.

The present invention further provides, within other aspects, methods for producing a DSP-12 polypeptide, comprising the steps of: (a) culturing a host cell as described above under conditions that permit expression of the DSP-12 polypeptide; and (b) isolating DSP-12 polypeptide from the host cell culture.

Also provided by the present invention are isolated antibodies, and antigen binding fragments thereof, that specifically bind to a DSP-12 polypeptide such as a polypeptide having the sequence of SEQ ID NO:2.

The present invention further provides, within other aspects, pharmaceutical compositions comprising a polypeptide, polynucleotide, antibody or fragment thereof as described above in combination with a physiologically acceptable carrier.

Within further aspects, the present invention provides methods for detecting DSP-12 expression in a sample, comprising: (a) contacting a sample with an antibody or an antigen-binding fragment thereof as described above, under conditions and for a time sufficient to allow formation of an antibody/DSP-12 complex; and (b) detecting the level of antibody/DSP-12 complex.

Within still other aspects, the present invention provides methods for detecting DSP-12 expression in a sample, comprising: (a) contacting a sample with an antisense polynucleotide as described above; and (b) detecting in the sample an amount of DSP-12 polynucleotide that hybridizes to the antisense polynucleotide. The amount of DSP-12 polynucleotide that hybridizes to the antisense polynucleotide may be determined, for example, using polymerase chain reaction or a hybridization assay.

The invention also provides DSP-12 polypeptides useful in screening assays for modulators of enzyme activity and/or substrate binding. Methods are also provided, within other aspects, for screening for an agent that modulates DSP-12 activity, comprising the steps of: (a) contacting a candidate agent with a polypeptide as described above, under conditions and for a time sufficient to permit interaction between the polypeptide and candidate agent; and (b) subsequently evaluating the ability of the polypeptide to dephosphorylate a DSP-12 substrate, relative to a predetermined ability of the polypeptide to dephosphorylate the DSP-12 substrate in the absence of candidate agent. Such methods may be performed in vitro or in a cellular environment (e.g., within an intact cell).

Within further aspects, methods are provided for screening for an agent that modulates DSP-12 activity, comprising the steps of: (a) contacting a candidate agent with a cell comprising a DSP-12 promoter operably linked to a polynucleotide encoding a detectable transcript or protein, under conditions and for a time sufficient to permit interaction between the promoter and candidate agent; and (b) subsequently evaluating the expression of the polynucleotide, relative to a predetermined level of expression in the absence of candidate agent.

Also provided are methods for modulating a proliferative response in a cell, comprising contacting a cell with an agent that modulates DSP-12 activity.

Within further aspects, methods are provided for modulating differentiation of a cell, comprising contacting a cell with an agent that modulates DSP-12 activity.

The present invention further provides methods for modulating cell survival, comprising contacting a cell with an agent that modulates DSP-12 activity.

Within related aspects, the present invention provides methods for treating a patient afflicted with a disorder associated with DSP-12 activity (or treatable by administration of DSP-12), comprising administering to a patient a therapeutically effective amount of an agent that modulates DSP-12 activity. Such disorders include Duchenne muscular dystrophy, cancer, graft-versus-host disease, autoimmune diseases, allergies, metabolic diseases, abnormal cell growth, abnormal cell proliferation and cell cycle abnormalities.

Within further aspects. DSP-12 substrate trapping mutant polypeptides are provided. Such polypeptides differ from the sequence recited in SEQ ID NO:2 in one or more amino acid deletions, additions, insertions or substitutions at no more than 50% of the residues in SEQ ID NO:2, such that the polypeptide binds to a substrate with an affinity that is not substantially diminished relative to DSP-12, and such that the ability of the polypeptide to dephosphorylate a substrate is reduced relative to DSP-12. Within certain specific embodiments, a substrate trapping mutant polypeptide contains a substitution at position 222 or position 253 of SEQ ID NO:2.

The present invention further provides, within other aspects, methods for screening a molecule for the ability to interact with DSP-12, comprising the steps of: (a) contacting a candidate molecule with a polypeptide as described above under conditions and for a time sufficient to permit the candidate molecule and polypeptide to interact; and (b) detecting the presence or absence of binding of the candidate molecule to the polypeptide. The step of detecting may comprise, for example, an affinity purification step, a yeast two hybrid screen or a screen of a phage display library.

In another aspect, the present invention provides isolated DSP-13 polypeptides having the sequence of DSP-13 recited in SEQ ID NO:6, or a variant thereof that differs in one or more amino acid deletions, additions, insertions or substitutions at no more than 50% of the residues in SEQ ID NO:6, such that the polypeptide retains the ability to dephosphorylate an activated MAP-kinase.

Within further aspects, the present invention provides an isolated polynucleotide that encodes at least ten consecutive amino acids of a polypeptide having a sequence corresponding to SEQ ID NO:6. In certain embodiments the invention provides an isolated polynucleotide that encodes at least fifteen consecutive amino acids of a polypeptide having a sequence corresponding to SEQ ID NO:6. Certain such polynucleotides encode a DSP-13 polypeptide. Still further, polynucleotides may be antisense polynucleotides that comprise at least 15 consecutive nucleotides complementary to a portion of a DSP-13 polynucleotide and/or that detectably hybridize to the complement of the sequence recited in SEQ ID NO:5 under conditions that include a wash in 0.1×SSC and 0.1% SDS at 60° C. for 15 minutes. Also provided are expression vectors comprising any of the foregoing polynucleotides, and host cells transformed or transfected with such expression vectors.

The present invention further provides, within other aspects, methods for producing a DSP-13 polypeptide, comprising the steps of: (a) culturing a host cell as described above under conditions that permit expression of the DSP-13 polypeptide: and (b) isolating DSP-13 polypeptide from the host cell culture.

Also provided by the present invention are isolated antibodies, and antigen binding fragments thereof, that specifically bind to a DSP-13 polypeptide such as a polypeptide having the sequence of SEQ ID NO:6.

The present invention further provides, within other aspects, pharmaceutical compositions comprising a polypeptide, polynucleotide, antibody or fragment thereof as described above in combination with a physiologically acceptable carrier.

Within further aspects, the present invention provides methods for detecting DSP-13 expression in a sample, comprising: (a) contacting a sample with an antibody or an antigen-binding fragment thereof as described above, under conditions and for a time sufficient to allow formation of an antibody/DSP-13 complex; and (b) detecting the level of antibody/DSP-13 complex.

Within still other aspects, the present invention provides methods for detecting DSP-13 expression in a sample, comprising: (a) contacting a sample with an antisense polynucleotide as described above; and (b) detecting in the sample an amount of DSP-13 polynucleotide that hybridizes to the antisense polynucleotide. The amount of DSP-13 polynucleotide that hybridizes to the antisense polynucleotide may be determined, for example, using polymerase chain reaction or a hybridization assay.

The invention also provides DSP-13 polypeptides useful in screening assays for modulators of enzyme activity and/or substrate binding. Methods are also provided, within other aspects, for screening for an agent that modulates DSP-13 activity, comprising the steps of: (a) contacting a candidate agent with a polypeptide as described above, under conditions and for a time sufficient to permit interaction between the polypeptide and candidate agent: and (b) subsequently evaluating the ability of the polypeptide to dephosphorylate a DSP-13 substrate, relative to a predetermined ability of the polypeptide to dephosphorylate the DSP-13 substrate in the absence of candidate agent. Such methods may be performed in vitro or in a cellular environment (e.g., within an intact cell).

Within further aspects, methods are provided for screening for an agent that modulates DSP-13 activity, comprising the steps of: (a) contacting a candidate agent with a cell comprising a DSP-13 promoter operably linked to a polynucleotide encoding a detectable transcript or protein, under conditions and for a time sufficient to permit interaction between the promoter and candidate agent; and (b) subsequently evaluating the expression of the polynucleotide, relative to a predetermined level of expression in the absence of candidate agent.

Also provided are methods for modulating a proliferative response in a cell, comprising contacting a cell with an agent that modulates DSP-13 activity.

Within further aspects, methods are provided for modulating differentiation of a cell, comprising contacting a cell with an agent that modulates DSP-13 activity.

The present invention further provides methods for modulating cell survival, comprising contacting a cell with an agent that modulates DSP-13 activity.

Within related aspects, the present invention provides methods for treating a patient afflicted with a disorder associated with DSP-13 activity (or treatable by administration of DSP-13), comprising administering to a patient a therapeutically effective amount of an agent that modulates DSP-13 activity. Such disorders include Duchenne muscular dystrophy, cancer, graft-versus-host disease, autoimmune diseases, allergies, metabolic diseases, abnormal cell growth, abnormal cell proliferation and cell cycle abnormalities.

Within further aspects, DSP-13 substrate trapping mutant polypeptides are provided. Such polypeptides differ from the sequence recited in SEQ ID NO:6 in one or more amino acid deletions, additions, insertions or substitutions at no more than 50% of the residues in SEQ ID NO:6, such that the polypeptide binds to a substrate with an affinity that is not substantially diminished relative to DSP-13, and such that the ability of the polypeptide to dephosphorylate a substrate is reduced relative to DSP-13. Within certain specific embodiments, a substrate trapping mutant polypeptide contains a substitution at position 368 or position 399 of SEQ ID NO:6.

The present invention further provides, within other aspects, methods for screening a molecule for the ability to interact with DSP-13, comprising the steps of: (a) contacting a candidate molecule with a polypeptide as described above under conditions and for a time sufficient to permit the candidate molecule and polypeptide to interact; and (b) detecting the presence or absence of binding of the candidate molecule to the polypeptide. The step of detecting may comprise, for example, an affinity purification step, a yeast two hybrid screen or a screen of a phage display library.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 presents a cDNA sequence for DSP-12 (SEQ ID NO:1), with the start and stop codons indicated in bold.

FIG. 2 presents the predicted amino acid sequence of DSP-12 (SEQ ID NO:2).

FIG. 3 presents a cDNA sequence for DSP-13 (SEQ ID NO:5), with the start and stop codons indicated in bold.

FIG. 4 presents the predicted amino acid sequence of DSP-13 (SEQ ID NO:6).

FIG. 5 shows a cDNA sequence for a DSP-13 alternate splice variant (SEQ ID NO:7), with the start and stop codons indicated in bold (FIG. 5A): FIG. 5B shows the predicted amino acid sequence (SEQ ID NO:8) of the DSP-13 alternate splice variant encoded by SEQ ID NO:7.

DETAILED DESCRIPTION OF THE INVENTION

Figure 6:
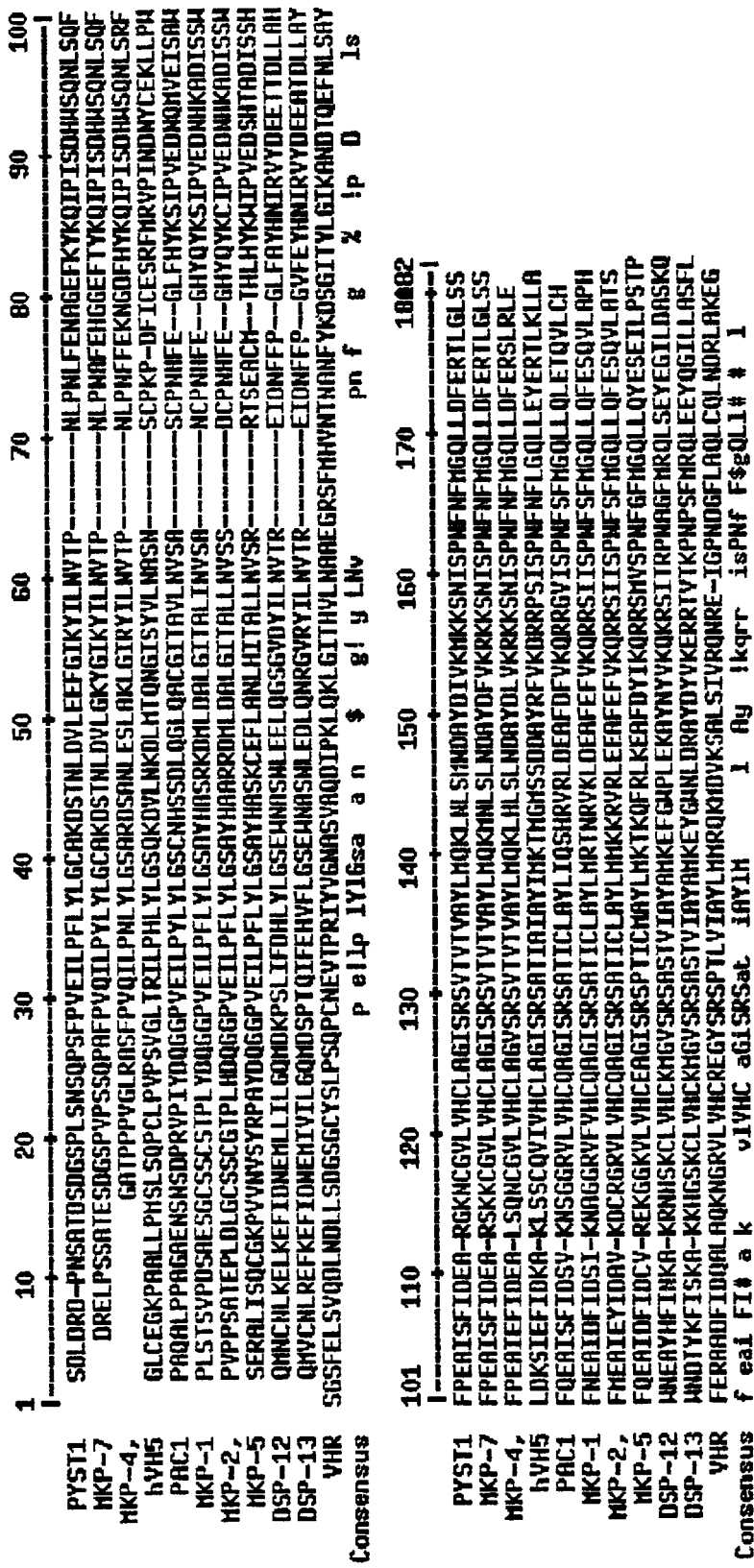
FIG. 6 is a sequence alignment showing sequence similarity between DSP-12, DSP-13 and other MAP-kinase phosphatases.

As noted above, the present invention is generally directed to compositions and methods for modulating (i.e., stimulating or inhibiting) cellular proliferative responses, in vitro and in vivo. In particular, the present invention provides dual-specificity phosphatases DSP-12 (FIGS. 1–2; SEQ ID NOs:1–2) and DSP-13 (FIGS. 3–4; SEQ ID NOs:5–6), as well as variants thereof and antibodies that specifically bind DSP-12 or DSP-13. Also provided herein are methods for using such compounds for screens, detection assays and related therapeutic uses.

DSP-12 AND DSP-13 Polypeptides and Polynucleotides

As used herein, the term "DSP-12 polypeptide" refers to a polypeptide that comprises a DSP-12 sequence as provided herein or a variant of such a sequence, and the term "DSP-13 polypeptide" refers to a polypeptide that comprises a DSP-13 sequence as provided herein or a variant of such a sequence. Such polypeptides are capable of dephosphorylating both tyrosine and threonine/serine residues in a DSP-12 or a DSP-13 substrate, with an activity that is not substantially diminished relative to that of a full length native DSP-12 or DSP-13. DSP-12 substrates and DSP-13 substrates include activated (i.e., phosphorylated) MAP-kinases. Other substrates may be identified using substrate trapping mutants, as described herein, and include polypeptides having one or more phosphorylated tyrosine, threonine and/or serine residues.

DSP-12 polypeptide variants and DSP-13 polypeptide variants within the scope of the present invention may contain one or more substitutions, deletions, additions and/or insertions. For certain DSP-12 and/or DSP-13 variants, the ability of the variant to dephosphorylate tyrosine and threonine residues within a DSP-12 substrate or a DSP-13 substrate is not substantially diminished. The ability of such a DSP-12 variant or a DSP-13 variant to dephosphorylate tyrosine and threonine residues within a DSP-12 substrate or a DSP-13 substrate may be enhanced or unchanged, relative to a native DSP-12 or a native DSP-13, or may be diminished by less than 50%, and preferably less than 20%, relative to native DSP-12 or DSP-13. Such variants may be identified using the representative assays provided herein.

Also contemplated by the present invention are modified forms of DSP-12 and/or DSP-13 in which a specific function is disabled. For example, such proteins may be constitutively active or inactive, or may display altered binding or catalytic properties. Such altered proteins may be generated using well known techniques, and the altered function confirmed using screens such as those provided herein. Certain modified DSP-12 and/or DSP-13 polypeptides are known as "substrate trapping mutants." Such polypeptides retain the ability to bind a substrate (i.e., $K_m$ is not substantially diminished), but display a reduced ability to dephosphorylate a substrate (i.e., $k_{cat}$ is reduced, preferably to less than 1 per minute). Further, the stability of the substrate trapping mutant/substrate complex should not be substantially diminished, relative to the stability of a DSP-12/substrate complex or a DSP-13/substrate complex. Complex stability may be assessed based on the association constant ($K_a$). Determination of $K_m$, $k_{cat}$ and $K_a$ may be readily accomplished using standard techniques known in the art (see, e.g., WO 98/04712; Lehninger, Biochemistry, 1975 Worth Publishers, NY) and assays provided herein. Substrate trapping mutants may be generated, for example, by modifying DSP-12 with an amino acid substitution at position 222 or position 253 (e.g., by replacing the amino acid aspartate at position 222 with an alanine residue, or by replacing the cysteine at residue 253 with a serine). Substrate trapping mutants may be generated, for example, by modifying DSP-13 with an amino acid substitution at position 368 or position 399 (e.g., by replacing the amino acid aspartate at position 368 with an alanine residue, or by replacing the cysteine at residue 399 with a serine). Substrate trapping mutants may be used, for example, to identify DSP-12 substrates or DSP-13 substrates. Briefly, the modified DSP-12 or DSP-13 may be contacted with a candidate substrate (alone or within a mixture of proteins, such as a cell extract) to permit the formation of a substrate/DSP-12 complex or a substrate/DSP-13 complex. The complex may then be isolated by conventional techniques to permit the isolation and characterization of substrate. The preparation and use of substrate trapping mutants is described, for example, within PCT Publication No. WO 98/04712.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, ser, thr; (2) cys, ser, tyr, thr, (3) val, ile, leu, met, ala, phe; (4) lys, arg, his; and (5) phe, tyr, trp, his. A variant may also, or alternatively, contain nonconservative changes.

In general, modifications may be more readily made in non-critical regions, which are regions of the native sequence that do not substantially change the activity of DSP-12 or DSP-13. Non-critical regions may be identified by modifying the DSP-12 or DSP-13 sequence in a particular region and assaying the ability of the resulting variant in a phosphatase assay, as described herein. Preferred sequence modifications are made so as to retain the active site domain (CLVHCKMGVSRSASTVIAYAM; SEQ ID NO:3). Within certain preferred embodiments, such modifications affect interactions between DSP-12 or DSP-13 and cellular components other than DSP-12 substrates or DSP-13 substrates. However, substitutions may also be made in critical regions of the native protein, provided that the resulting variant substantially retains the ability to stimulate substrate dephosphorylation. Within certain embodiments, a variant contains substitutions, deletions, additions and/or insertions at no more than 50%, preferably no more than 25%, of the amino acid residues.

Variants may also (or alternatively) be modified by, for example, the deletion or addition of amino acids that have minimal influence on the activity of the polypeptide. In particular, variants may contain additional amino acid sequences at the amino and/or carboxy termini. Such sequences may be used, for example, to facilitate purification or detection of the polypeptide.

DSP-12 and/or DSP-13 polypeptides may be prepared using any of a variety of well known techniques. Recombinant polypeptides encoded by DNA sequences as described below may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells, and forms that differ in glycosylation may be generated by varying the host cell or post-isolation processing. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield. *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

A "DSP-12 polynucleotide" is any polynucleotide that encodes at least a portion of a DSP-12 polypeptide or a variant thereof, or that is complementary to such a polynucleotide. A "DSP-13 polynucleotide" is any polynucleotide that encodes at least a portion of a DSP-13 polypeptide or a variant thereof, or that is complementary to such a polynucleotide. Preferred polynucleotides comprise at least 15 consecutive nucleotides, preferably at least 30 consecutive nucleotides, that encode a DSP-12 polypeptide or a DSP-13 polypeptide or that are complementary to such a sequence. Certain polynucleotides encode a DSP-12 polypeptide or a DSP-13 polypeptide; others may find use as probes, primers or antisense oligonucleotides, as described below. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

DSP-12 polynucleotides and/or DSP-13 polynucleotides may comprise a native sequence (i.e., an endogenous DSP-12 or DSP-13 sequence or a portion or splice variant thereof) or may comprise a variant of such a sequence. Polynucleotide variants may contain one or more substitutions, additions, deletions and/or insertions such that the activity of the encoded polypeptide is not substantially diminished, as described above. The effect on the activity of the encoded polypeptide may generally be assessed as described herein. Variants preferably exhibit at least about 70% identity, more preferably at least about 80% identity and most preferably at least about 90% identity to a polynucleotide sequence that encodes a native DSP-12 or a portion thereof, or to a polynucleotide sequence that encodes a native DSP-13 or a portion thereof. The percent identity may be readily determined by comparing sequences using computer algorithms well known to those of ordinary skill in the art, such as Align or the BLAST algorithm (Altschul, *J. Mol. Biol.* 219:555–565, 1991; Henikoff and Henikoff, *Proc. Natl. Acad. Sci. USA* 89:10915–10919, 1992), which is available at the NCBI website (http://www/ncbi.nlm.nih.gov/cgi-bin/BLAST). Default parameters may be used. Certain variants are substantially homologous to a native gene. Such polynucleotide variants are capable of hybridizing under moderately stringent conditions to a naturally occurring DNA or RNA sequence encoding a native DSP-12 (or a complementary sequence) or a native DSP-13 (or a complementary sequence). Suitable moderately stringent conditions include prewashing in a solution of 5×SSC, 0.5% SDS. 1.0 mM EDTA (pH 8.0); hybridizing at 50° C.–65° C. 5×SSC, overnight; followed by washing twice at 65° C. for 20 minutes with each of 2×, 0.5× and 0.2×SSC containing 0.1% SDS. For additional stringency, conditions may include a wash in 0.1×SSC and 0.1% SDS at 60° C. for 15 minutes.

It will be appreciated by those having ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Polynucleotides may be prepared using any of a variety of techniques. For example, a polynucleotide may be amplified from cDNA prepared from a suitable cell or tissue type, such as human brain, testis, kidney or skeletal muscle. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., human brain, testis, kidney, liver or skeletal muscle cDNA) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library may then be screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. Clones may be analyzed to determine the amount of additional sequence by, for example, PCR using a primer from the partial sequence and a primer from the vector. Restriction maps and partial sequences may be generated to identify one or more overlapping clones. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. One such technique is known as "rapid amplification of cDNA ends" or RACE. This technique involves the use of an internal primer and an external primer, which hybridizes to a polyA region or vector sequence, to identify sequences that are 5' and 3' of a known sequence. Any of a variety of commercially available kits may be used to perform the amplification step. Primers may be designed using, for example, software well known in the art. Primers are preferably 17–32 nucleotides in length, have a GC content of at least 40% and anneal to the target sequence at temperatures of about 54° C. to 72° C. The amplified region may be sequenced as described above, and overlapping sequences assembled into a contiguous sequence.

A cDNA sequence encoding DSP-12 is provided in FIG. 1 (SEQ ID NO:1), and the predicted amino acid sequence is provided in FIG. 2 (SEQ ID NO:2). The DSP-12 active site (CLVHCKMGVSRSASTVIAYAM; SEQ ID NO:3) is located at positions 249 through 269 of SEQ ID NO:2 (FIG. 7). Sequence information immediately adjacent to this site was used to design 5' and 3' RACE reactions with human skeletal muscle and testis cDNA to identify a 1,656 base pair cDNA that corresponds to a mRNA that is ubiquitously expressed in a variety of tissues examined. This cDNA encodes a protein of 552 amino acids that is referred to herein as DSP-12. DSP-12 shows significant homology to other MAP-kinase phosphatases, as shown by the sequence comparison presented in FIG. 6.

A cDNA sequence encoding DSP-13 is provided in FIG. 3 (SEQ ID NO:5), and the predicted amino acid sequence is provided in FIG. 4 (SEQ ID NO:6). The DSP-13 active site (CLVHCKMGVSRSASTVIAYAM; SEQ ID NO:3), is located at positions 395 through 415 of SEQ ID NO:6 (FIG. 7). Sequence information immediately adjacent to this site was used to design 5' and 3' RACE reactions with human skeletal muscle and testis cDNA to identify a 1,527 base pair cDNA that corresponds to a mRNA that is ubiquitously expressed in a variety of tissues examined. This cDNA encodes a protein of 509 amino acids that is referred to herein as DSP-13. DSP-13 shows significant homology to other MAP-kinase phosphatases, as shown by the sequence comparison presented in FIG. 6. An alternate splice variant of DSP-13 is encoded by a 723 base pair cDNA, which encodes a protein of 241 amino acids (FIG. 5).

DSP-12 polynucleotide variants and DSP-13 polynucleotide variants may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Alternatively, RNA molecules may be generated by in vitro or in vivo transcription of DNA sequences encoding DSP-12 and/or DSP-13, or portion thereof, provided that the DNA is incorporated into a vector with a suitable RNA polymerase promoter (such as T7 or SP6). Certain polynucleotides may be used to prepare an encoded polypeptide, as described herein. In addition, or alternatively, a polynucleotide may be administered to a patient such that the encoded polypeptide is generated in vivo.

A polynucleotide that is complementary to at least a portion of a coding sequence (e.g., an antisense polynucleotide or a ribozyme) may also be used as a probe or primer, or to modulate gene expression. Identification of oligonucleotides and ribozymes for use as antisense agents, and DNA encoding genes for their targeted delivery, involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g. Agrwal et al., *Tetrahedron Lett.* 28:3539–3542 (1987); Miller et al., *J. Am. Chem. Soc.* 93:6657–6665 (1971); Stec et al., *Tetrahedron Lett.* 26:2191–2194 (1985); Moody et al., *Nucl. Acids Res.* 12:4769–4782 (1989); Uznanski et al., *Nucl. Acids Res.* (1989); Letsinger et al. *Tetrahedron* 40:137–143 (1984); Eckstein, *Annu. Rev. Biochem.* 54:367–402 (1985), Eckstein, *Trends Biol. Sci.* 14:97–100 (1989); Stein In: *Oligodeoxynucleotides, Antisense Inhibitors of Gene Expression*, Cohen, Ed, Macmillan Press, London, pp. 97–117 (1989); Jager et al., *Biochemistry* 27:7237–7246 (1988)).

Antisense polynucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl Acids Res.* 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

Particularly useful antisense nucleotides and triplex molecules are molecules that are complementary to or bind the sense strand of DNA or mRNA that encodes a DSP-12 polypeptide or a DSP-13 polypeptide or a protein mediating any other process related to expression of endogenous DSP-12 and/or DSP-13, such that inhibition of translation of mRNA encoding the DSP-12 polypeptide or the DSP-13 polypeptide is affected. cDNA constructs that can be transcribed into antisense RNA may also be introduced into cells or tissues to facilitate the production of antisense RNA. Antisense technology can be used to control gene expression through interference with binding of polymerases, transcription factors or other regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a DSP-12 gene or a DSP-13 gene (e.g., promoter, enhancer or transcription initiation site), and block transcription of the gene; or to block translation by inhibiting binding of a transcript to ribosomes.

The present invention also contemplates DSP-12-specific and DSP-13-specific ribozymes. A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). Any DSP-12 mRNA-specific ribozyme of DSP-13 mRNA-specific ribozyme, or a nucleic acid encoding such a ribozyme, may be delivered to a host cell to effect inhibition of DSP-12 or DSP-13 gene expression. Ribozymes may therefore be delivered to the host cells by DNA encoding the ribozyme linked to a eukaryotic promoter, such as a eukaryotic viral promoter, such that upon introduction into the nucleus, the ribozyme will be directly transcribed.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a suitable vector contains an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector using well known techniques. A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Within other aspects, a DSP-12 promoter or a DSP-13 promoter may be isolated using standard techniques. The present invention provides nucleic acid molecules comprising such a promoter or one or more cis- or trans-acting regulatory elements thereof. Such regulatory elements may enhance or suppress expression of DSP-12 or DSP-13. A 5' flanking region may be generated using standard techniques, based on the genomic sequence provided herein. If necessary, additional 5' sequences may be generated using PCR-based or other standard methods. The 5' region may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer. Suitable reporter genes may include genes encoding luciferase, beta-galactosidase, chloramphenicol acetyl transferase, secreted alkaline phosphatase or the Green Fluorescent Protein gene. Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of DSP-12 and/or DSP-13 expression. In general, the construct with the minimal 5' flanking region showing the highest level of expression of reporter gene is identified as the promoter. Such promoter regions may be linked to a reporter gene and used to evaluate agents for the ability to modulate DSP-12 and/or DSP-13 transcription.

Once a functional promoter is identified, cis- and trans-acting elements may be located. Cis-acting sequences may generally be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated.

The present invention also contemplates the use of allelic variants of DSP-12 and DSP-13, as well as DSP-12 and DSP-13 sequences from other organisms. Such sequences may generally be identified based upon similarity to the sequences provided herein (e.g., using hybridization techniques) and based upon the presence of DSP-12 activity and/or DSP-13 activity, using an assay provided herein.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Assays for Detecting DSP-12 and DSP-13 Activity

DSP-12 polypeptide variants may be tested for DSP-12 activity, and DSP-13 polypeptide variants may be tested for DSP-13 activity, using any suitable assay for MAP-kinase phosphatase activity. Such assays may be performed in vitro or within a cell-based assay. For example, a MAP-kinase may be obtained in inactive form from Upstate Biotechnology (Lake Placid, N.Y.; catalog number 14-198). Phosphorylation of the MAP-kinase can be performed using well known techniques (such as those described by Zheng and Guan, *J. Biol. Chem* 268:16116–16119, 1993) using the MAP-kinase kinase MEK-1 (available from Upstate Biotechnology; cat. no. 14-206). Radiolabeled substrate may be used for the kinase reaction, resulting in radiolabeled, activated MAP-kinase. A DSP-12 polypeptide or a DSP-13 polypeptide may then be tested for the ability to dephosphorylate the activated MAP-kinase by contacting the DSP-12 or DSP-13 polypeptide with the MAP-kinase under suitable conditions (e.g., Tris, pH 7.5, 1 mM EDTA, 1 mM dithiothreitol, 1 mg/mL bovine serum albumin for 10 minutes at 30° C.; or as described by Zheng and Guan, *J. Biol. Chem.* 268:16116–16119, 1993). Dephosphorylation of the MAP-kinase may be detected using any of a variety of assays, such as a coupled kinase assay (evaluating phosphorylation of a MAP-kinase substrate using any assay generally known in the art) or directly, based on (1) the loss of radioactive phosphate groups (e.g., by gel electrophoresis, followed by autoradiography); (2) the shift in electrophoretic mobility following dephosphorylation; (3) the loss of reactivity with an antibody specific for phosphotyrosine or phosphothreonine; or (4) a phosphoamino acid analysis of the MAP-kinase. Certain assays may generally be performed as described by Ward et al., *Nature* 367:651–654, 1994 or Alessi et al., *Oncogene* 8:2015–2020, 1993. In general, contact of 500 pg-50 ng of DSP-12 or DSP-13 polypeptide with 100 ng-100 µg activated MAP-kinase should result in a detectable dephosphorylation of the MAP-kinase, typically within 20–30 minutes. Within certain embodiments, 0.01–10 units/mL (preferably about 0.1 units/mL, where a unit is an amount sufficient to dephosphorylate 1 nmol substrate per minute) DSP-12 or DSP-13 polypeptide may be contacted with 0.1–10 µM (preferably about 1 µM) activated MAP-kinase to produce a detectable dephosphorylation of a MAP-kinase. Preferably, a DSP-12 or DSP-13 polypeptide results in dephosphorylation of a MAP-kinase or a phosphorylated substrate (such as a tyrosine- and/or serine-phosphorylated peptide) that is at least as great as the dephosphorylation observed in the presence of a comparable amount of native human DSP-12 or DSP-13. It will be apparent that other substrates identified using a substrate trapping mutant as described herein may be substituted for the MAP-kinase within such assays.

Antibodies and Antigen-Binding Fragments

Also contemplated by the present invention are peptides, polypeptides and other non-peptide molecules that specifically bind to DSP-12 or to DSP-13. As used herein, a molecule is said to "specifically bind" to DSP-12 if it reacts at a detectable level with DSP-12, and does not react detectably with peptides containing an unrelated sequence or a sequence of a different dual-specificity phosphatase. Similarly, a molecule is said to "specifically bind" to DSP-13 if it reacts at a detectable level with DSP-13, and does not react detectably with peptides containing an unrelated sequence or a sequence of a different dual-specificity phosphatase. Such binding properties may generally be assessed using an ELISA, which may be readily performed by those of ordinary skill in the art. Preferred binding molecules include antibodies (which may be, for example, polyclonal, monoclonal, single chain, chimeric, anti-idiotypic or CDR-grafted). Certain preferred antibodies are those antibodies that inhibit or block DSP-12 and/or DSP-13 activity within an in vitro assay, as described herein.

Antibodies may generally be prepared by any of a variety of techniques using isolated native or recombinant DSP-12 protein, or recombinant DSP-13 protein, as antigen. Such techniques are known to those having ordinary skill in the art (see, e.g., Harlow and Lane, *Antibodies: A Laboratory Manual*, Cold Spring Harbor Laboratory, 1988). In one such technique, an immunogen comprising a DSP-12 polypeptide (or a DSP-13 polypeptide) is initially injected into a suitable animal (e.g., mice, rats, rabbits, sheep and goats), preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for DSP-12 or a variant thereof, or for DSP-13 or a variant thereof, may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred. Hybridomas that generate monoclonal antibodies that specifically bind to DSP-12 (or that specifically bind to DSP-13) are contemplated by the present invention.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Within certain embodiments, the use of antigen-binding fragments of antibodies may be preferred. Such fragments include Fab fragments, which may be prepared using standard techniques (e.g., by digestion with papain to yield Fab and Fc fragments). The Fab and Fc fragments may be separated by affinity chromatography (e.g., on protein A bead columns), using standard techniques.

Polyclonal and monoclonal antibodies may be used for the affinity isolation of DSP-12 or DSP-13 polypeptides. Techniques for affinity purification of a polypeptide are well known in the art (see, e.g., Hermanson, G. T. et al. "Immobilized Affinity Ligand Techniques," Academic Press, Inc. (New York, 1992)). Briefly, an antibody or antigen-binding fragment thereof may be immobilized on a solid support material, which is then contacted with a sample comprising the polypeptide of interest. Following separation from the remainder of the sample, the polypeptide is then released from the immobilized antibody.

Methods for Detecting DSP-12 and DSP-13 Expression

Certain aspects of the present invention provide methods that employ antibodies raised against DSP-12 or DSP-13, or hybridizing polynucleotides, for diagnostic and assay purposes. Certain assays involve using an antibody or other agent to detect the presence or absence of DSP-12 or DSP-13, or proteolytic fragments thereof. Alternatively, nucleic acid encoding DSP-12 or DSP-13 may be detected, using standard hybridization and/or PCR techniques. Suitable probes and primers may be designed by those having ordinary skill in the art based on the DSP-12 and DSP-13 cDNA sequences provided herein. Assays may generally be performed using any of a variety of samples obtained from a biological source, such as eukaryotic cells, bacteria, viruses, extracts prepared from such organisms and fluids found within living organisms. Biological samples that may be obtained from a patient include blood samples, biopsy specimens, tissue explants, organ cultures and other tissue or cell preparations. A patient or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, a patient may be suspected of having or being at risk for having a disease associated with altered cellular signal transduction, or may be known to be free of a risk for or presence of such as disease.

To detect DSP-12 protein or DSP-13 protein, the reagent is typically an antibody, which may be prepared as described below. There are a variety of assay formats known to those having ordinary skill in the art for using an antibody to detect a polypeptide in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target DSP-12 (or DSP-13) and remove it from the remainder of the sample. The bound DSP-12 (or DSP-13) may then be detected using a second antibody or reagent that contains a reporter group. Alternatively, a competitive assay may be utilized, in which a DSP-12 or DSP-13 polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the level of DSP-12 or DSP-13 in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of DSP-12 or DSP-13 in a sample is a two-antibody sandwich assay. This assay may be performed by first contacting an antibody that has been immobilized on a solid support, commonly the well of a microtiter plate, with the biological sample, such that DSP-12 (or DSP-13) within the sample is allowed to bind to the immobilized antibody (a 30 minute incubation time at room temperature is generally sufficient). Unbound sample is then removed from the immobilized DSP-12/antibody complexes (or DSP-13/antibody complexes) and a second antibody (containing a reporter group such as an enzyme, dye, radionuclide, luminescent group, fluorescent group or biotin) capable of binding to a different site on the DSP-12 (or DSP-13) is added. The amount of second antibody that remains bound to the solid support is then determined using a method appropriate for the specific reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of DSP-12 or DSP-13 in a sample, using well known techniques.

In a related aspect of the present invention, kits for detecting DSP-12 (or DSP-13) and DSP-12 (or DSP-13) phosphatase activity are provided. Such kits may be designed for detecting the level of DSP-12 (or DSP-13) or nucleic acid encoding DSP-12 (or DSP-13), or may detect phosphatase activity of DSP-12 (or DSP-13) in a direct phosphatase assay or a coupled phosphatase assay. In general, the kits of the present invention comprise one or more containers enclosing elements, such as reagents or buffers, to be used in the assay.

A kit for detecting the level of DSP-12 (or DSP-13), or nucleic acid encoding DSP-12 (or DSP-1 3) typically contains a reagent that binds to the DSP-12 (or DSP-13) protein, DNA or RNA. To detect nucleic acid encoding DSP-12 (or DSP-13), the reagent may be a nucleic acid probe or a PCR primer. To detect DSP-12 or DSP-13 protein, the reagent is typically an antibody. Such kits also contain a reporter group suitable for direct or indirect detection of the reagent (i.e., the reporter group may be covalently bound to the reagent or may be bound to a second molecule, such as Protein A. Protein G, immunoglobulin or lectin, which is itself capable of binding to the reagent). Suitable reporter groups include, but are not limited to, enzymes (e.g., horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

Kits for detecting DSP-12 activity typically comprise a DSP-12 substrate in combination with a suitable buffer; similarly, kits for detecting DSP-13 activity typically comprise a DSP-13 substrate in combination with a suitable buffer. DSP-12 activity or DSP-13 activity may be specifically detected by performing an immunoprecipitation step with a DSP-12-specific (or a DSP-13-specific) antibody prior to performing a phosphatase assay as described above. Other reagents for use in detecting dephosphorylation of substrate may also be provided.

Within certain diagnostic assays, a proliferative disorder may be detected in a patient based on the presence of an altered DSP-12 or DSP-13, or an altered level of DSP-12 expression or of DSP-13 expression. For example, an antibody may distinguish between a wild-type DSP-12 and an altered DSP-12 having a variation in amino acid sequence, or between a wild-type DSP-13 and an altered DSP-13 having a variation in amino acid sequence. Such a variation may be indicative of the presence of a proliferative disorder, or of susceptibility to such a disorder. Hybridization and amplification techniques may be similarly used to detect modified DSP-12 or DSP-13 sequences.

Methods for Identifying Modulators of DSP-12 and DSP-13 Activity

In one aspect of the present invention, DSP-12 or DSP-13 polypeptides may be used to identify agents that modulate DSP activity. Such agents may inhibit or enhance signal transduction via a MAP-kinase cascade, leading to cell proliferation. An agent that modulates DSP-12 or DSP-13 activity may alter expression and/or stability of DSP-12 or DSP-13, DSP-12 or DSP-13 protein activity and/or the ability of DSP-12 or DSP-13 to dephosphorylate a substrate. Agents that may be screened within such assays include, but are not limited to, antibodies and antigen-binding fragments thereof, competing peptides that represent, for example, a catalytic site or a dual phosphorylation motif, antisense polynucleotides and ribozymes that interfere with transcription and/or translation of DSP-12 or DSP-13 and other natural and synthetic molecules, for example small molecule inhibitors, that bind to and inactivate DSP-12 or DSP-13.

Candidate agents for use in a method of screening for a modulator of DSP-12 or DSP-13 according to the present invention may be provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a plurality of samples, each containing at least one DSP-12 or DSP-13 polypeptide as provided herein, and then assayed for their ability to enhance or inhibit DSP-12- or DSP-13-mediated dephosphorylation of, or binding to, a substrate. Compounds so identified as capable of influencing DSP-12 or DSP-13 function (e.g., phosphotyrosine and/or phosphoserine/threonine dephosphorylation) are valuable for therapeutic and/or diagnostic purposes, since they permit treatment and/or detection of diseases associated with DSP-12 or DSP-13 activity. Such compounds are also valuable in research directed to molecular signaling mechanisms that involve DSP-12 or DSP-13, and to refinements in the discovery and development of future DSP-12 or DSP-13 compounds exhibiting greater specificity.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694 PCT/US91/04666, which are hereby incorporated by reference in their entireties) or other compositions that may include small molecules as provided herein (see e.g., PCT/US94/08542, EP 0774464, U.S. Pat. No. 5,798,035, U.S. 5,789,172, U.S. 5,751,629, which are hereby incorporated by reference in their entireties). Those having ordinary skill in the art will appreciate that a diverse assortment of such libraries may be prepared according to established procedures, and tested using DSP-12 and/or DSP-13 according to the present disclosure.

In certain embodiments, modulating agents may be identified by combining a candidate agent with a DSP-12 or DSP-13 polypeptide or a polynucleotide encoding such a polypeptide, in vitro or in vivo, and evaluating the effect of the candidate agent on the DSP-12 or DSP-13 phosphatase activity using, for example, a representative assay described herein. An increase or decrease in phosphatase activity can be measured by performing a representative assay provided herein in the presence and absence of a candidate agent. Briefly, a candidate agent may be included in a mixture of active DSP-12 or DSP-13 polypeptide and substrate (e.g., a phosphorylated MAP-kinase), with or without pre-incubation with one or more components of the mixture. In general, a suitable amount of antibody or other agent for use in such an assay ranges from about 0.01 µM to about 100 µM. The effect of the agent on DSP-12 or DSP-13 activity may then be evaluated by quantitating the loss of phosphate from the substrate, and comparing the loss with that achieved using DSP-12 or DSP-13 without the addition of a candidate agent. Alternatively, a coupled kinase assay may be used, in which DSP-12 or DSP-13 activity is indirectly measured based on MAP-kinase activity.

Alternatively, a polynucleotide comprising a DSP-12 promoter operably linked to a DSP-12 coding region or reporter gene may be used to evaluate the effect of a test compound on DSP-12 transcription. Similarly, a polynucleotide comprising a DSP-13 promoter operably linked to a DSP-13 coding region or reporter gene may be used to evaluate the effect of a test compound on DSP-13 transcription. Such assays may be performed in cells that express DSP-12 or DSP-13 endogenously (e.g., human kidney or liver) or in cells transfected with an expression vector comprising a DSP-12 promoter or a DSP-13 promoter linked to a reporter gene. The effect of a test compound may then be evaluated by assaying the effect on transcription of DSP-12 (or DSP-13) or the reporter using, for example, a Northern blot analysis or a suitable reporter activity assay.

DSP-12 or DSP-13 activity may also be measured in whole cells transfected with a reporter gene whose expression is dependent upon the activation of an appropriate substrate. For example, appropriate cells (i.e., cells that express DSP-12 or DSP-13) may be transfected with a substrate-dependent promoter linked to a reporter gene. In such a system, expression of the reporter gene (which may be readily detected using methods well known to those of ordinary skill in the art) depends upon activation of substrate. Dephosphorylation of substrate may be detected based on a decrease in reporter activity. Candidate modulating agents may be added to such a system, as described above, to evaluate their effect on DSP-12 or DSP-13 activity.

The present invention further provides methods for identifying a molecule that interacts with, or binds to, DSP-12 or DSP-13. Such a molecule generally associates with DSP-12 or DSP-13 with an affinity constant ($K_a$) of at least $10^4$, preferably at least $10^5$, more preferably at least $10^6$, still more preferably at least $10^7$ and most preferably at least $10^8$. Affinity constants may be determined using well known techniques. Methods for identifying interacting molecules may be used, for example, as initial screens for modulating agents, or to identify factors that are involved in the in vivo DSP-12 or DSP-13 activity. Techniques for substrate trapping of DSP-12 or DSP-13 variants are also included. In addition to standard binding assays, there are many other techniques that are well known for identifying interacting molecules, including yeast two-hybrid screens, phage display and affinity techniques. Such techniques may be performed using routine protocols, which are well known to those of ordinary skill in the art (see, e.g., Bartel et al. In *Cellular Interactions in Development: A Practical Approach*, D. A. Harley, ed., Oxford University Press (Oxford, UK), pp. 153–179, 1993). Within these and other techniques, proteins may be phosphorylated prior to assaying for interacting proteins.

Within other aspects, the present invention provides animal models in which an animal either does not express a functional DSP-12 (or DSP-13), or expresses an altered DSP-12 (or DSP-13). Such animals may be generated using standard homologous recombination strategies. Animal models generated in this manner may be used to study activities of DSP-12 or DSP-13 polypeptides and modulating agents in vivo.

Methods for Dephosphorylating a Substrate

In another aspect of the present invention, a DSP-12 polypeptide may be used for dephosphorylating a substrate of DSP-12, or a DSP-13 polypeptide may be used for dephosphorylating a substrate of DSP-13. In one embodiment, a substrate may be dephosphorylated in vitro by incubating a DSP-12 or DSP-13 polypeptide with a substrate in a suitable buffer (e.g., Tris, pH 7.5.1 mM EDTA, 1 mM dithiothreitol, 1 mg/mL bovine serum albumin) for 10 minutes at 30° C. Any compound that can be dephosphorylated by DSP-12 or DSP-13, such as a MAP-kinase, may be used as a substrate. In general, the amounts of the reaction components may range from about 50 pg to about 50 ng of DSP-12 or DSP-13 polypeptide and from about 10 ng to about 10 µg of substrate. Dephosphorylated substrate may then be purified, for example, by affinity techniques and/or gel electrophoresis. The extent of substrate dephosphorylation may generally be monitored by adding [$\gamma$-$^{32}$P]labeled substrate to a test aliquot, and evaluating the level of substrate dephosphorylation as described herein.

Methods for Modulating Cellular Responses

Modulating agents may be used to modulate cellular responses such as cell proliferation, differentiation and survival, in a variety of contexts, both in vivo and in vitro. In general, to modulate such a response, a cell is contacted with an agent that modulates DSP-12 or DSP-13 activity, under conditions and for a time sufficient to permit modulation of DSP-12 or DSP-13 activity. Agents that modulate a cellular response may function in any of a variety of ways. For example, an agent may modulate a pattern of gene expression (i.e., may enhance or inhibit expression of a family of genes or genes that are expressed in a coordinated fashion). A variety of hybridization and amplification techniques are available for evaluating patterns of gene expression. Alternatively, or in addition, an agent may affect apoptosis or necrosis of the cell, and/or may modulate the functioning of the cell cycle within the cell. (See, e.g., Ashkenazi et al., 1998 *Science,* 281:1305; Thornberry et al. 1998 *Science* 281:1312; Evan et al., 1998 *Science* 281:1317; Adams et al., 1998 *Science* 281:1322; and references cited therein.)

Cells treated as described above may display standard characteristics of cells with altered proliferation, differentiation or survival. In addition, such cells may (but need not) display other detectable properties, such as contact inhibition of cell growth, anchorage independent growth or altered intercellular adhesion. Such properties may be detected using techniques that are well known in the art.

Therapeutic Methods

One or more DSP-12 or DSP-13 polypeptides, modulating agents and/or polynucleotides encoding such polypeptides and/or modulating agents may also be used to modulate DSP-12 or DSP-13 activity in a patient. As used herein, a "patient" may be any mammal, including a human, and may be afflicted with a condition associated with DSP-12 or DSP-13 activity or may be free of detectable disease.

Accordingly, the treatment may be of an existing disease or may be prophylactic. Conditions associated with DSP-12 or DSP-13 activity include any disorder associated with cell proliferation, including Duchenne muscular dystrophy, cancer, graft-versus-host disease (GVHD), autoimmune diseases, allergy or other conditions in which immunosuppression may be involved, metabolic diseases, abnormal cell growth or proliferation and cell cycle abnormalities. Certain such disorders involve loss of normal MAP-kinase phosphatase activity, leading to uncontrolled cell growth. DSP-12 or DSP-13 polypeptides, and polynucleotides encoding such polypeptides, can be used to ameliorate such disorders.

For administration to a patient, one or more polypeptides, polynucleotides and/or modulating agents are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate or compounds may be encapsulated within liposomes using well known technology. Pharmaceutical compositions within the scope of the present invention may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. 1985). In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

For pharmaceutical compositions comprising a polynucleotide encoding a DSP-12 or DSP-13 polypeptide and/or modulating agent (such that the polypeptide and/or modulating agent is generated in situ), the polynucleotide may be present within any of a variety of delivery systems known to those of ordinary skill in the art, including nucleic acid, and bacterial, viral and mammalian expression systems. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

Within a pharmaceutical composition, a DSP-12 or DSP-13 polypeptide, polynucleotide or modulating agent may be linked to any of a variety of compounds. For example, such an agent may be linked to a targeting moiety (e.g., a monoclonal or polyclonal antibody, a protein or a liposome) that facilitates the delivery of the agent to the target site. As used herein, a "targeting moiety" may be any substance (such as a compound or cell) that, when linked to an agent enhances the transport of the agent to a target cell or tissue, thereby increasing the local concentration of the agent. Targeting moieties include antibodies or fragments thereof, receptors, ligands and other molecules that bind to cells of, or in the vicinity of, the target tissue. An antibody targeting agent may be an intact (whole) molecule, a fragment thereof, or a functional equivalent thereof. Examples of antibody fragments are F(ab')2, –Fab'. Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) at which the agent is expected to exert a therapeutic benefit.

Pharmaceutical compositions may be administered in a manner appropriate to the disease to be treated (or prevented). An appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival). For prophylactic use, a dose should be sufficient to prevent, delay the onset of or diminish the severity of a disease associated with cell proliferation.

Optimal dosages may generally be determined using experimental models and/or clinical trials. In general, the amount of polypeptide present in a dose, or produced in situ by DNA present in a dose, ranges from about 0.01 μg to about 100 μg per kg of host, typically from about 0.1 μg to about 10 μg. The use of the minimum dosage that is sufficient to provide effective therapy is usually preferred. Patients may generally be monitored for therapeutic or prophylactic effectiveness using assays suitable for the condition being treated or prevented, which will be familiar to those of ordinary skill in the art. Suitable dose sizes will vary with the size of the patient, but will typically range from about 10 mL to about 500 mL for 10–60 kg animal.

The following Examples are offered by way of illustration and not by way of limitation.

EXAMPLES

Example 1

Cloning and Sequencing cDNA Encoding DSP-12 and DSP-13

This Example illustrates the cloning of cDNA molecules encoding human DSP-12 and DSP-13.

A conserved sequence motif defining a novel homology domain of dual-specificity phosphatases was identified as follows: Dual specificity phosphatases belong to the larger family of protein tyrosine phosphatases (PTPs) that share a conserved catalytic domain containing a cysteine residue situated N-terminal to a stretch of five variable amino acids followed by an arginine residue (Fauman et al. *Trends In Bioch. Sci.* 21:413–417, 1996). DSPs typically contain a PTP active site motif but lack sequence homology to PTPs in other regions (Jia, *Biochem, and Cell Biol* 75:17–26, 1997). There is, however, no reported consensus sequence that is conserved among DSPs, nor is a consensus region apparent from examination of the known DSP sequences such as those referred to above. To derive a longer consensus DSP amino acid sequence motif that would be useful for the identification of new DSP family members, multiple known human dual-specificity phosphatases sequences were aligned and compared. From an alignment of nine amino acid sequences derived from nine particular human DSPs having MAP-kinase phosphatase activity (FIG. 6), a candidate conserved homology region was identified. This homology region consisted of a 24-amino acid peptide sequence, based on analysis of the DSP regions, situated on either side of, and including, the PTP active site signature motif (including the conserved catalytic domain at positions 123–129 of FIG. 6). Thus, a candidate peptide having the sequence:

NGRVLVHCQAGISRSGTNILAYLM SEQ ID NO:4 was used to search the High Throughput Genomic Sequences (HTGS) database (Nat. Center for Biol. Information, www.ncbi.nlm.nih.gov/BLAST). The search employed an algorithm (tblastn) capable of reverse translation of the candidate peptide with iterations allowing for genetic code degeneracy within default, parameters. The search results identified a portion (nucleotides at positions numbers 54301 to 55500) of the HTGS entry having the accession number HTGS AC008081 as a candidate MAP-kinase phosphatase sequence encoding a MAP kinase phosphatase catalytic domain. HTGS AC008081 did not include a complete coding region of an expressed gene such as a gene encoding a DSP-12 having MAP-kinase phosphatase activity, nor were the sense strand and open reading frame identified.

To verify that the identified portion of the HTGS AC008081 sequence exists as an expressed sequence (i.e., as transcribed mRNA) in tissues expressing DSP-12, RT-PCR was performed using human cDNA reverse transcribed from human skeletal muscle and testis RNA. The cDNA was screened in 5' and 3' RACE (rapid amplification of cDNA ends) reactions as described (Frohman et al. *Proc. Nat. Acad. Sci. USA* 85:8998, 1988; Ohara et al. *Proc. Nat. Acad Sci USA* 86:5673, 1989; Loh et al. *Science* 243:217, 1989) using 5'/3' RACE kits (Clontech, Palo Alto. Calif.; Life Technologies, Inc., Gaithersburg, Md.) according to the supplier's instructions, with the following primers:

DSP12-GSP1:

5'-GGCTGCTGGAGGCTGCTGTCTGTCTGC-3' SEQ ID NO:9

DSP12-SP4:

5'-CCC AAC GCG GGG CTT TAT GAG GCA GC-3' SEQ ID NO:10

RACE products were amplified from the cDNA using these primers, indicating that sequences complementary to the portion of HTGS AC008081 idenitifed in the tblastn search were present in the cDNA. Sequence information upstream and downstream from the conserved sequence motif of HTGS AC008081 was then used in additional 5' and 3' RACE reactions with human cDNA. using the following primers (SEQ ID NOS:11 to 16):

DSP12-GSP2:

5'-GCCACAGCTTGTTGTGCCGCTGTTTGC-3' SEQ ID NO:11

DSP12-GSP3:

5'-GCATTCCATTCAGAGCCGAGATAAAGATGATC GAA-3' SEQ ID NO:12

DSP12-GSP4:

5'-GGAGCTTGGCTTTGATGAGGCGCTCGG-3' SEQ ID NO:13

DSP12revGSP1:

5'-GCA GAC AGA CAG CAG CCT CCA GCA GCC-3' SEQ ID NO:14

DSP12-SP6:

5'-GGTGGAGGAGACGGAAAGGGAGGAGGGC-3' SEQ ID NO:15

DSP12-SP7:

5'-GGGAGCAGGGAGGTGGGGGCAGCTT-3' SEQ ID NO:16

Sequences of the resulting RACE products indicated the presence in the cDNA of an open reading frame (FIG. 1, SEQ ID NO:1) encoding a DSP-12 polypeptide of 552 amino acids (FIG. 2, SEQ ID NO:2).

Repeating the HTGS database search with the DSP-12 catalytic domain sequence, as described above using the tblastn algorithm, indicated that portions of the genomic DNA sequence database entry having accession number HTGS AC007919 could also encode portions of the DSP-12 polypeptide sequence. Additionally, searching the HTGS database with the DSP-12 active site domain amino acid sequence as described above identified potential DSP-12 partial coding sequences in a portion (nucleotides at positions numbers 114961 to 116040) of a genomic DNA sequence database entry having accession number HTGS AC010189. Alignment of DSP-12 cDNA (SEQ ID NO:1) and HTGS AC010189, however, revealed an unexpected degree of sequence divergence on either side of the regions of high homology (FIG. 7). Sequence analysis of HTGS AC010189 was therefore performed to determine potential DSP coding regions of AC010189, and the following primers were prepared for 5'/3' RACE screening of human cDNA (reverse transcribed from human skeletal muscle) as described above:

DSP13-GSP1:
  5'-CTCTTCCAGTTGTCTCATGAAGCTTGGGTT GGG-3' SEQ ID NO:17
DSP13-GSP2:
  5'-GGGCTTGGTTACCGTTCGTCTTTCTTTCACAT AGTCA-3' SEQ ID NO:18
DSP13-GSP3:
  5-GGATCACTATCATTTCATTGTCTATAAATTCCTT GAATTCCCGC-3' SEQ ID NO:19
DSP13-GSP4:
  5'-TGA ATT CCC GCA AGT TGCACACCATTTG-3' SEQ ID NO:20
DSP13-SP4:
  5'-GGA ATA TGG CTG GAA TCT GGA CCG AGC CTA TGA-3' SEQ ID NO:21
DSP13-SP5:
  5'-TGTGAAAGAAAGACGAACGGTAACCAAGCC CAA C-3' SEQ ID NO:22

Sequences of the resulting RACE products indicated the presence of an open reading frame (FIG. 3, SEQ ID NO:5) encoding a distinct polypeptide referred to herein as DSP-13. The DSP-13 polypeptide is homologous to, but distinct from, DSP-12. A DSP-13 polypeptide of 509 amino acids is shown in FIG. 4 (SEQ ID NO:6). Additional RACE products that were obtained and sequenced revealed the presence of a DSP-13 alternate splice variant, the DNA sequence (FIG. 5A, SEQ ID NO:7) and 241 amino acid polypeptide sequence (FIG. 5B, SEQ ID NO:8) of which are shown in FIG. 5.

Figure 7:
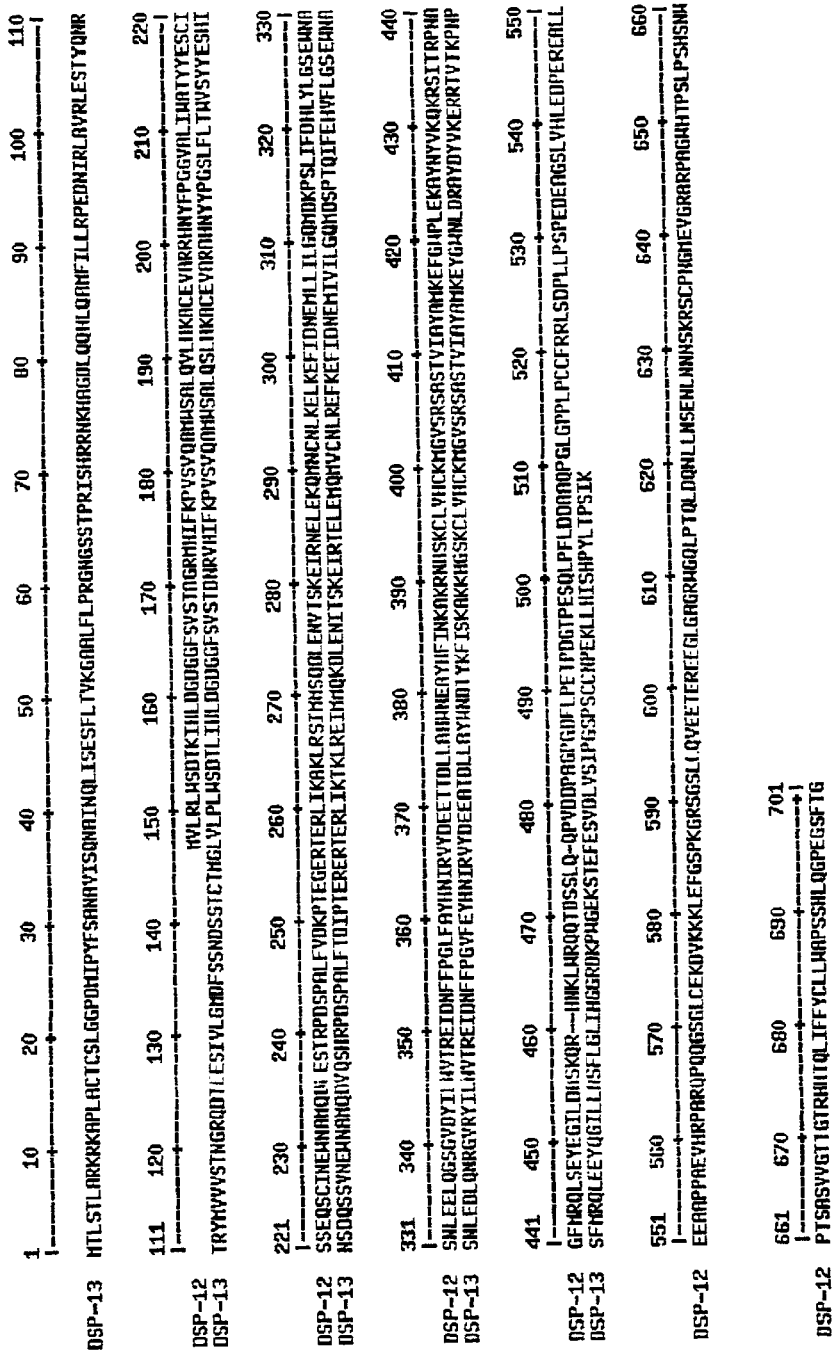
FIG. 7 is a sequence alignment of full length DSP-12 (SEQ ID NO:2) and DSP-13 (SEQ ID NO:6) amino acid sequences.

The sequences of DSP-12 and DSP-13 had significant homology to other MAP-kinase phosphatases (FIG. 6). DSP-12 and DSP-13 share a common active site domain (FIG. 7, positions 395–415) having the amino acid sequence:

CLVHCKMGVSRSASTVIAYAM SEQ ID NO:3

Semiquantitative RT-PCR analyses were performed. These analyses showed detectable DSP-12 and DSP-13 encoding mRNAs in RNA samples from all human tissues analyzed, including brain, thymus, placenta, skeletal muscle, heart, liver, pancreas, testes and adipose tissue.

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

What is claimed is:

1. An isolated polynucleotide that encodes a polypeptide comprising an amino acid sequence set fourth in SEQ ID NO:2.

2. An expression vector comprising a polynucleotide according to claim 1.

3. A host cell transformed or transfected with an expression vector according to claim 2.

4. An isolated polynucleotide comprising the sequence set fourth in SEQ ID NO:1.

5. An isolated polynucleotide, wherein the isolated polynucleotide exhibits at least 90% nucleotide identity to a polynucleotide comprising the sequence set forth in SEQ ID NO:1, and wherein the isolated polynucleotide encodes a polypeptide capable of dephosphorylating an activated mitogen-activated protein kinase (MAP-kinase), said polypeptide comprising the peptide sequence CLVHCKMGVSRSASTVIAYAM (SEQ ID NO:3).

6. An expression vector comprising a polynucleotide according to claim 5.

7. A host cell transformed or transfected with an expression vector according to claim 6.

8. A method of producing a dual specificity phosphatase 12 (DSP-12) polypeptide, comprising the steps of:
   (a) culturing a host cell according to claim 7 under conditions that permit expression of the DSP-12 polypeptide; and
   (b) isolating DSP-12 polypeptide from the host cell culture.

9. An isolated polynucleotide that encodes a polypeptide capable of dephosphorylating an activated mitogen-activated protein kinase (MAP-kinase), said polynucleotide comprising a sequence that encodes the peptide sequence CLVHCKMGVSRSASTVIAYAM (SEQ ID NO:3) and that is at least 90% identical to a polynucleotide that encodes a polypeptide comprising an amino acid sequence set forth in SEQ ID NO:2.

10. An isolated polynucleotide that encodes a polypeptide capable of dephosphorylating an activated mitogen-activated protein kinase (MAP-kinase), said polypeptide comprising an amino acid sequence of SEQ ID NO:2, wherein aspartic acid is located at position 222 and the peptide sequence CLVHCKMGVSRSASTVIAYAM (SEQ ID NO:3) is located at positions 249 through 269 of SEQ ID NO:2, wherein said polynucleotide comprises a sequence at least 90% identical to a polynucleotide that encodes a polypeptide comprising the amino acid sequence of SEQ ID NO:2.

11. An expression vector comprising a polynucleotide according to any one of claims 4, 9, and 10.

12. A host cell transformed or transfected with an expression vector according to claim 9.

13. An antisense polynucleotide comprising a polynucleotides that is complementary to a polynucleotide according to any one of claims 1, 4, 9, and 10.

* * * * *

UNITED STATES PATENT AND TRADEMARK OFFICE
CERTIFICATE OF CORRECTION

PATENT NO. : 6,902,919 B2
DATED : June 7, 2005
INVENTOR(S) : Ralf M. Luche et al.

It is certified that error appears in the above-identified patent and that said Letters Patent is hereby corrected as shown below:

Title page,
Item [56], References Cited, OTHER PUBLICATIONS,
"Jia, "Protein Phosphatases: Structures and Implications," *Biochem. Cell. Biol.* 75(1):17-26." should read as
-- Jia, "Protein Phosphatases: Structures and Implications," *Biochem. Cell. Biol.* 75(1):17-26, 1997 --.

Column 54,
Line 62, "claim 9" should read as -- claim 11 --.

Signed and Sealed this

Twenty-ninth Day of November, 2005

JON W. DUDAS
*Director of the United States Patent and Trademark Office*

SEQUENCE LISTING

<160> NUMBER OF SEQ ID NOS: 33

<210> SEQ ID NO 1
<211> LENGTH: 1949
<212> TYPE: DNA
<213> ORGANISM: Homo sapiens

<400> SEQUENCE: 1

```
aagcagtggt aacaacgcag agtacgcggg cgaggagaat atcttgctgg gagtggactt      60
ttccagtaag gaaagtaaaa gctgcaccat tgggatggtt ctccgactgt ggagcgacac     120
gaaaatccac cttgatggag atggtgggtt cagcgtgagc acagcaggaa ggatgcacat     180
atttaagcct gtgtctgtcc aggccatgtg gtctgccctg caggtgcttc acaaggcctg     240
cgaagtggcc cggaggcaca actacttccc cgggggtgta gctctcatct gggctaccta     300
ctatgagagc tgcatcagct ccgagcagag ctgcatcaac gagtggaacg ccatgcagga     360
cctggagtct acgcggcccg actccccgc gctatttgtg gacaagccca ctgaagggga     420
aaggaccgag cgcctcatca aagccaagct ccgaagcatc atgatgagcc aggatctaga     480
aaatgtgact tccaaagaga ttcgtaatga attagagaaa cagatgaatt gtaacttgaa     540
ggaactcaag gaatttatag acaatgagat gctacttatc ttgggacaga tggacaagcc     600
ctcccttatc ttcgatcatc tttatctcgg ctctgaatgg aatgcatcca atctggagga     660
actgcagggc tcaggggttg attacatttt aaatgttacc agagaaatcg ataatttttt     720
tcctggctta tttgcatatc ataacatccg agtctacgat gaagagacca cagacctcct     780
cgcccactgg aatgaagcgt atcattttat aaacaaagcg aagaggaacc attccaagtg     840
cctggtgcat tgcaaaatgg gcgtgagtcg ctcggcctcc acagtcatag cctatgcaat     900
```

```
gaaggaattc ggctggcctc tggaaaaagc atataactat gtaaagcaga agcgcagcat    960
cacgcgcccc aacgcgggct ttatgaggca gctgtctgag tatgaaggca tcttggatgc   1020
aagcaaacag cggcacaaca agctgtggcg tcagcagaca gacagcagcc tccagcagcc   1080
tgtggatgac cctgcaggac ctggcgactt cttgccagag accccagatg cacccggga    1140
aagccagctg cccttcttgg atgatgccgc ccagcccggc ttagggcccc cctcccctg    1200
ctgtttccgg cgactctcag accccttct gccttcccct gaggatgaag ccggcagctt    1260
ggtccacctg gaggatccgg agagggaggc tctgttggag gaagctgctc cacctgcaga   1320
ggtgcacagg ccggccagac agccccagca aggttccgga ctctgtgaga aggatgtgaa   1380
gaagaaacta gagtttggga gtcccaaagg tcggagcggc tccttgctgc aggtggagga   1440
gacggaaagg gaggagggcc tgggagcagg gaggtggggg cagcttccaa cccagctcga   1500
tcaaaacctg ctcaactcgg agaacctaaa caacaacagc aagaggagct gtcccaacgg   1560
catggaggta ggcagagccc ggcctgcagg gtggcacacc ccatcccttc catcccactc   1620
taattggcct acctcagcct ctgtagtagg gactacaggc acccgccacc acacccagct   1680
gattttttc tattgtctcc tctgggcccc cagctcccat ctccagggac ctgagggttc    1740
tttcacaggg tgattctgct ggtgggtacg tagtgcatac cttatatagc aaattgagaa   1800
tctgttggga ataacacata tctctgcaca ccatcttcac cccatgtacc ttattcatac   1860
cctgggcagg gcttccaact caatttcttt ttgtgtatgt aaaattaaaa catataattt   1920
atcagccaaa aaaaaaaaaa aaaaaaaaa                                     1949
```

<210> SEQ ID NO 2
<211> LENGTH: 552
<212> TYPE: PRT
<213> ORGANISM: Homo sapien

<400> SEQUENCE: 2

```
Met Val Leu Arg Leu Trp Ser Asp Thr Lys Ile His Leu Asp Gly Asp
 1               5                  10                  15

Gly Gly Phe Ser Val Ser Thr Ala Gly Arg Met His Ile Phe Lys Pro
            20                  25                  30

Val Ser Val Gln Ala Met Trp Ser Ala Leu Gln Val Leu His Lys Ala
        35                  40                  45

Cys Glu Val Ala Arg Arg His Asn Tyr Phe Pro Gly Gly Val Ala Leu
    50                  55                  60

Ile Trp Ala Thr Tyr Tyr Glu Ser Cys Ile Ser Ser Glu Gln Ser Cys
65                  70                  75                  80

Ile Asn Glu Trp Asn Ala Met Gln Asp Leu Glu Ser Thr Arg Pro Asp
                85                  90                  95

Ser Pro Ala Leu Phe Val Asp Lys Pro Thr Glu Gly Glu Arg Thr Glu
            100                 105                 110

Arg Leu Ile Lys Ala Lys Leu Arg Ser Ile Met Met Ser Gln Asp Leu
        115                 120                 125

Glu Asn Val Thr Ser Lys Glu Ile Arg Asn Glu Leu Glu Lys Gln Met
    130                 135                 140

Asn Cys Asn Leu Lys Glu Leu Lys Glu Phe Ile Asp Asn Glu Met Leu
145                 150                 155                 160

Leu Ile Leu Gly Gln Met Asp Lys Pro Ser Leu Ile Phe Asp His Leu
                165                 170                 175

Tyr Leu Gly Ser Glu Trp Asn Ala Ser Asn Leu Glu Glu Leu Gln Gly
```

-continued

```
                180             185             190
Ser Gly Val Asp Tyr Ile Leu Asn Val Thr Arg Glu Ile Asp Asn Phe
            195                 200                 205
Phe Pro Gly Leu Phe Ala Tyr His Asn Ile Arg Val Tyr Asp Glu Glu
    210                 215                 220
Thr Thr Asp Leu Leu Ala His Trp Asn Glu Ala Tyr His Phe Ile Asn
225                 230                 235                 240
Lys Ala Lys Arg Asn His Ser Lys Cys Leu Val His Cys Lys Met Gly
                245                 250                 255
Val Ser Arg Ser Ala Ser Thr Val Ile Ala Tyr Ala Met Lys Glu Phe
            260                 265                 270
Gly Trp Pro Leu Glu Lys Ala Tyr Asn Tyr Val Lys Gln Lys Arg Ser
    275                 280                 285
Ile Thr Arg Pro Asn Ala Gly Phe Met Arg Gln Leu Ser Glu Tyr Glu
    290                 295                 300
Gly Ile Leu Asp Ala Ser Lys Gln Arg His Asn Lys Leu Trp Arg Gln
305                 310                 315                 320
Gln Thr Asp Ser Ser Leu Gln Gln Pro Val Asp Pro Ala Gly Pro
                325                 330                 335
Gly Asp Phe Leu Pro Glu Thr Pro Asp Gly Thr Pro Glu Ser Gln Leu
            340                 345                 350
Pro Phe Leu Asp Asp Ala Ala Gln Pro Gly Leu Gly Pro Pro Leu Pro
    355                 360                 365
Cys Cys Phe Arg Arg Leu Ser Asp Pro Leu Leu Pro Ser Pro Glu Asp
    370                 375                 380
Glu Thr Gly Ser Leu Val His Leu Glu Asp Pro Glu Arg Glu Ala Leu
385                 390                 395                 400
Leu Glu Glu Ala Ala Pro Pro Ala Glu Val His Arg Pro Ala Arg Gln
                405                 410                 415
Pro Gln Gln Gly Ser Gly Leu Cys Glu Lys Asp Val Lys Lys Leu
            420                 425                 430
Glu Phe Gly Ser Pro Lys Gly Arg Ser Gly Ser Leu Leu Gln Val Glu
    435                 440                 445
Glu Thr Glu Arg Glu Glu Gly Leu Gly Ala Gly Arg Trp Gly Gln Leu
    450                 455                 460
Pro Thr Gln Leu Asp Gln Asn Leu Leu Asn Ser Glu Asn Leu Asn Asn
465                 470                 475                 480
Asn Ser Lys Arg Ser Cys Pro Asn Gly Met Glu Val Gly Arg Ala Arg
                485                 490                 495
Pro Ala Gly Trp His Thr Pro Ser Leu Pro Ser His Ser Asn Trp Pro
            500                 505                 510
Thr Ser Ala Ser Val Val Gly Thr Thr Gly Thr Arg His His Thr Gln
    515                 520                 525
Leu Ile Phe Phe Tyr Cys Leu Leu Trp Ala Pro Ser Ser His Leu Gln
    530                 535                 540
Gly Pro Glu Gly Ser Phe Thr Gly
545                 550
```

<210> SEQ ID NO 3
<211> LENGTH: 21
<212> TYPE: PRT
<213> ORGANISM: Homo sapien

<400> SEQUENCE: 3

Cys Leu Val His Cys Lys Met Gly Val Ser Arg Ser Ala Ser Thr Val
1               5                  10                  15

Ile Ala Tyr Ala Met
            20

<210> SEQ ID NO 4
<211> LENGTH: 24
<212> TYPE: PRT
<213> ORGANISM: Artificial Sequence
<220> FEATURE:
<223> OTHER INFORMATION: Derivered from the alignment of nine particular
      human DSPs having MAP-kinase phosphatase activity

<400> SEQUENCE: 4

Asn Gly Arg Val Leu Val His Cys Gln Ala Gly Ile Ser Arg Ser Gly
1               5                  10                  15

Thr Asn Ile Leu Ala Tyr Leu Met
            20

<210> SEQ ID NO 5
<211> LENGTH: 1711
<212> TYPE: DNA
<213> ORGANISM: Homo sapiens

<400> SEQUENCE: 5

| | | | | | |
|---|---|---|---|---|---|
| cctgggaaga | agttatctat | ctctcgagtg | acattcaaga | tataccgtac | ccctcggttc | 60 |
| tgtaagtcct | ctaagttgga | ggcattccat | tctgagccgg | ccccatgacc | ctgagcacgt | 120 |
| tggcccgcaa | gaggaaggcg | cccctcgctt | gcacctgcag | cctcggtggc | cccgacatga | 180 |
| ttccttactt | ctccgccaac | gcggtcatct | cgcagaacgc | catcaaccag | ctcatcagcg | 240 |
| agagctttct | aactgtcaaa | ggtgctgccc | tttttctacc | acggggaaat | ggctcatcca | 300 |
| caccaagaat | cagccacaga | cggaacaagc | atgcaggcga | tctccaacag | catctccaag | 360 |
| caatgttcat | tttactccgc | ccagaagaca | acatcaggct | ggctgtaaga | ctggaaagta | 420 |
| cttaccagaa | tcgaacacgc | tatatggtag | tggtttcaac | taatggtaga | caagacactg | 480 |
| aagaaagcat | cgtcctagga | atggatttct | cctctaatga | cagtagcact | tgtaccatgg | 540 |
| gcttagtttt | gcctctctgg | agcgacacgc | taattcattt | ggatggtgat | ggtgggttca | 600 |
| gtgtatcgac | ggataacaga | gttcacatat | tcaaacctgt | atctgtgcag | gcaatgtggt | 660 |
| ctgcactaca | gagcttacac | aaggcttgtg | aagtcgccag | agcgcataac | tactacccag | 720 |
| gcagcctatt | tctcacttgg | gtgagttatt | atgagagcca | tatcaactca | gatcaatcct | 780 |
| cagtcaatga | atggaatgca | atgcaagatg | tacagtccca | ccggcccgac | tctccagctc | 840 |
| tcttcaccga | catacctact | gaacgtgaac | gaacagaaag | gctaattaaa | accaaattaa | 900 |
| gggagatcat | gatgcagaag | gatttggaga | atattacatc | caaagagata | agaacagagt | 960 |
| tggaaatgca | aatggtgtgc | aacttgcggg | aattcaagga | atttatagac | aatgaaatga | 1020 |
| tagtgatcct | tggtcaaatg | gatagcccta | cacagatatt | tgagcatgtg | ttcctgggct | 1080 |
| cagaatggaa | tgcctccaac | ttagaggact | tacagaaccg | aggggtacgg | tatatcttga | 1140 |
| atgtcactcg | agagatagat | aacttcttcc | caggagtctt | tgagtatcat | aacattcggg | 1200 |
| tatatgatga | agaggcaacg | gatctcctgg | cgtactggaa | tgacacttac | aaattcatct | 1260 |
| ctaaagcaaa | gaaacatgga | tctaaatgcc | ttgtgcactg | caaaatgggg | gtgagtcgct | 1320 |
| cagcctccac | cgtgattgcc | tatgcaatga | aggaatatgg | ctggaatctg | gaccgagcct | 1380 |
| atgactatgt | gaaagaaaga | cgaacggtaa | ccaagcccaa | cccaagcttc | atgagacaac | 1440 |

-continued

```
tggaagagta tcaggggatc ttgctggcaa gcttcctagg cttgattcat ggagggaggg    1500
acaagccctg gggagagaaa agcacagaat ttgagtcagt agatctggtt tccattcctg    1560
gttcaccctc ttgctgcaac cctgagaagt tacttcacat ttctcatcct tacctgaccc    1620
catctataaa atgaaaatca agagatccat ctcacagggt tattgtgaat aaaaatgtgt    1680
ttgaatgttt ataaaaaaaa aaaaaaaaa a                                    1711
```

<210> SEQ ID NO 6
<211> LENGTH: 509
<212> TYPE: PRT
<213> ORGANISM: Homo sapiens

<400> SEQUENCE: 6

```
Met Thr Leu Ser Thr Leu Ala Arg Lys Arg Lys Ala Pro Leu Ala Cys
  1               5                  10                  15

Thr Cys Ser Leu Gly Gly Pro Asp Met Ile Pro Tyr Phe Ser Ala Asn
             20                  25                  30

Ala Val Ile Ser Gln Asn Ala Ile Asn Gln Leu Ile Ser Glu Ser Phe
         35                  40                  45

Leu Thr Val Lys Gly Ala Ala Leu Phe Leu Pro Arg Gly Asn Gly Ser
     50                  55                  60

Ser Thr Pro Arg Ile Ser His Arg Arg Asn Lys His Ala Gly Asp Leu
 65                  70                  75                  80

Gln Gln His Leu Gln Ala Met Phe Ile Leu Arg Pro Glu Asp Asn
                 85                  90                  95

Ile Arg Leu Ala Val Arg Leu Glu Ser Thr Tyr Gln Asn Arg Thr Arg
                100                 105                 110

Tyr Met Val Val Ser Thr Asn Gly Arg Gln Asp Thr Glu Glu Ser
            115                 120                 125

Ile Val Leu Gly Met Asp Phe Ser Ser Asn Asp Ser Ser Thr Cys Thr
        130                 135                 140

Met Gly Leu Val Leu Pro Leu Trp Ser Asp Thr Leu Ile His Leu Asp
145                 150                 155                 160

Gly Asp Gly Gly Phe Ser Val Ser Thr Asp Asn Arg Val His Ile Phe
                165                 170                 175

Lys Pro Val Ser Val Gln Ala Met Trp Ser Ala Leu Gln Ser Leu His
            180                 185                 190

Lys Ala Cys Glu Val Ala Arg Ala His Asn Tyr Tyr Pro Gly Ser Leu
        195                 200                 205

Phe Leu Thr Trp Val Ser Tyr Tyr Glu Ser His Ile Asn Ser Asp Gln
    210                 215                 220

Ser Ser Val Asn Glu Trp Asn Ala Met Gln Asp Val Gln Ser His Arg
225                 230                 235                 240

Pro Asp Ser Pro Ala Leu Phe Thr Asp Ile Pro Thr Glu Arg Glu Arg
                245                 250                 255

Thr Glu Arg Leu Ile Lys Thr Lys Leu Arg Glu Ile Met Met Gln Lys
            260                 265                 270

Asp Leu Glu Asn Ile Thr Ser Lys Glu Ile Arg Thr Glu Leu Glu Met
        275                 280                 285

Gln Met Val Cys Asn Leu Arg Glu Phe Lys Glu Phe Ile Asp Asn Glu
    290                 295                 300

Met Ile Val Ile Leu Gly Gln Met Asp Ser Pro Thr Gln Ile Phe Glu
305                 310                 315                 320

His Val Phe Leu Gly Ser Glu Trp Asn Ala Ser Asn Leu Glu Asp Leu
```

```
                325                 330                 335
Gln Asn Arg Gly Val Arg Tyr Ile Leu Asn Val Thr Arg Glu Ile Asp
            340                 345                 350

Asn Phe Phe Pro Gly Val Phe Glu Tyr His Asn Ile Arg Val Tyr Asp
            355                 360                 365

Glu Glu Ala Thr Asp Leu Leu Ala Tyr Trp Asn Asp Thr Tyr Lys Phe
            370                 375                 380

Ile Ser Lys Ala Lys Lys His Gly Ser Lys Cys Leu Val His Cys Lys
385                 390                 395                 400

Met Gly Val Ser Arg Ser Ala Ser Thr Val Ile Ala Tyr Ala Met Lys
            405                 410                 415

Glu Tyr Gly Trp Asn Leu Asp Arg Ala Tyr Asp Tyr Val Lys Glu Arg
            420                 425                 430

Arg Thr Val Thr Lys Pro Asn Pro Ser Phe Met Arg Gln Leu Glu Glu
            435                 440                 445

Tyr Gln Gly Ile Leu Leu Ala Ser Phe Leu Gly Leu Ile His Gly Gly
            450                 455                 460

Arg Asp Lys Pro Trp Gly Glu Lys Ser Thr Glu Phe Glu Ser Val Asp
465                 470                 475                 480

Leu Val Ser Ile Pro Gly Ser Pro Ser Cys Cys Asn Pro Glu Lys Leu
            485                 490                 495

Leu His Ile Ser His Pro Tyr Leu Thr Pro Ser Ile Lys
            500                 505

<210> SEQ ID NO 7
<211> LENGTH: 1052
<212> TYPE: DNA
<213> ORGANISM: Homo sapiens

<400> SEQUENCE: 7
ctgcccggct tctaacaggc cactgaccgg tactcactgg ggacccacgc tctaagttgt      60
tgatctctag aaccgatttt ggaaaaggat ttgccttatt gaagaagaca ggatcattct     120
tctttctttc ccatttaaga ataatcgtta ttaagaatat cgtttaagaa taatcgttat     180
ttctctcttc tcagacctac tgaacgtgaa cgaacagaaa ggctaattaa aaccaaatta     240
agggagatca tgatgcagaa ggatttggag aatattacat ccaaagagat aagaacagag     300
ttggaaatgc aaatggtgtg caacttgcgg gaattcaagg aatttataga caatgaaatg     360
atagtgatcc ttggtcaaat ggatagccct acacagatat ttgagcatgt gttcctgggc     420
tcagaatgga atgcctccaa cttagaggac ttacagaacc gagggtacg gtatatcttg     480 aatgtcactc gagagataga taacttcttc ccaggagtct tgagtatca aacattcgg      540 gtatatgatg aagaggcaac ggatctcctg gcgtactgga atgacactta caaattcatc     600
tctaaagcaa agaaacatgg atctaaatgc cttgtgcact gcaaaatggg ggtgagtcgc     660
tcagcctcca ccgtgattgc ctatgcaatg aaggaatatg gctggaatct ggaccgagcc     720
tatgactatg tgaaagaaag acgaacggta accaagccca acccaagctt catgagacaa     780
ctggaagagt atcaggggat cttgctggca agcttcctag gcttgattca tggagggagg     840
gacaagccct ggggagagaa aagcacagaa tttgagtcag tagatctggt ttccattcct     900
ggttcaccct cttgctgcaa ccctgagaag ttacttcaca tttctcatcc ttacctgacc     960
ccatctataa aatgaaaatc aagagatcca tctcacaggg ttattgtgaa taaaaatgtg    1020

tttgaatgtt tataaaaaaa aaaaaaaaaa aa                                   1052
```

```
<210> SEQ ID NO 8
<211> LENGTH: 241
<212> TYPE: PRT
<213> ORGANISM: Homo sapiens

<400> SEQUENCE: 8

Met Met Gln Lys Asp Leu Glu Asn Ile Thr Ser Lys Glu Ile Arg Thr
1               5                   10                  15

Glu Leu Glu Met Gln Met Val Cys Asn Leu Arg Glu Phe Lys Glu Phe
            20                  25                  30

Ile Asp Asn Glu Met Ile Val Ile Leu Gly Gln Met Asp Ser Pro Thr
        35                  40                  45

Gln Ile Phe Glu His Val Phe Leu Gly Ser Glu Trp Asn Ala Ser Asn
50                  55                  60

Leu Glu Asp Leu Gln Asn Arg Gly Val Arg Tyr Ile Leu Asn Val Thr
65                  70                  75                  80

Arg Glu Ile Asp Asn Phe Phe Pro Gly Val Phe Glu Tyr His Asn Ile
                85                  90                  95

Arg Val Tyr Asp Glu Glu Ala Thr Asp Leu Leu Ala Tyr Trp Asn Asp
            100                 105                 110

Thr Tyr Lys Phe Ile Ser Lys Ala Lys Lys His Gly Ser Lys Cys Leu
        115                 120                 125

Val His Cys Lys Met Gly Val Ser Arg Ser Ala Ser Thr Val Ile Ala
130                 135                 140

Tyr Ala Met Lys Glu Tyr Gly Trp Asn Leu Asp Arg Ala Tyr Asp Tyr
145                 150                 155                 160

Val Lys Glu Arg Arg Thr Val Thr Lys Pro Asn Pro Ser Phe Met Arg
                165                 170                 175

Gln Leu Glu Glu Tyr Gln Gly Ile Leu Leu Ala Ser Phe Leu Gly Leu
            180                 185                 190

Ile His Gly Gly Arg Asp Lys Pro Trp Gly Lys Ser Thr Glu Phe
        195                 200                 205

Glu Ser Val Asp Leu Val Ser Ile Pro Gly Ser Pro Ser Cys Cys Asn
    210                 215                 220

Pro Glu Lys Leu Leu His Ile Ser His Pro Tyr Leu Thr Pro Ser Ile
225                 230                 235                 240

Lys

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ggctgctgga ggctgctgtc tgtctgc                                              27

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
cccaacgcgg ggctttatga ggcagc                                               26
```

-continued

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
gccacagctt gttgtgccgc tgtttgc                          27

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
gcattccatt cagagccgag ataaagatga tcgaa                 35

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
ggagcttggc tttgatgagg cgctcgg                          27

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
gcagacagac agcagcctcc agcagcc                          27

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
ggtggaggag acggaaaggg aggagggc                         28

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
gggagcaggg aggtgggggc agctt                            25

<210> SEQ ID NO 17
<211> LENGTH: 33
<212> TYPE: DNA
<213> ORGANISM: Artificial Sequence
<220> FEATURE:
<223> OTHER INFORMATION: Primer -continued

<400> SEQUENCE: 17
ctcttccagt tgtctcatga agcttgggtt ggg                                  33

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
gggcttggtt accgttcgtc tttctttcac atagtca                              37

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
ggatcactat catttcattg tctataaatt ccttgaattc ccgc                      44

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
tgaattcccg caagttgcac accatttg                                        28

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
ggaatatggc tggaatctgg accgagccta tga                                  33

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
tgtgaaagaa agacgaacgg taaccaagcc caac                                 34

<210> SEQ ID NO 23
<211> LENGTH: 170
<212> TYPE: PRT
<213> ORGANISM: Homo sapiens

<400> SEQUENCE: 23

Ser Asp Leu Asp Arg Asp Pro Asn Ser Ala Thr Asp Ser Asp Gly Ser
 1               5                  10                  15

Pro Leu Ser Asn Ser Gln Pro Ser Phe Pro Val Glu Ile Leu Pro Phe
            20                  25                  30

```
Leu Tyr Leu Gly Cys Ala Lys Asp Ser Thr Asn Leu Asp Val Leu Glu
            35                  40                  45

Glu Phe Gly Ile Lys Tyr Ile Leu Asn Val Thr Pro Asn Leu Pro Asn
 50                  55                  60

Leu Phe Glu Asn Ala Gly Glu Phe Lys Tyr Lys Gln Ile Pro Ile Ser
 65                  70                  75                  80

Asp His Trp Ser Gln Asn Leu Ser Gln Phe Phe Pro Glu Ala Ile Ser
                85                  90                  95

Phe Ile Asp Glu Ala Arg Gly Lys Asn Cys Gly Val Leu Val His Cys
            100                 105                 110

Leu Ala Gly Ile Ser Arg Ser Val Thr Val Thr Val Ala Tyr Leu Met
            115                 120                 125

Gln Lys Leu Asn Leu Ser Met Asn Asp Ala Tyr Asp Ile Val Lys Met
130                 135                 140

Lys Lys Ser Asn Ile Ser Pro Asn Phe Asn Phe Met Gly Gln Leu Leu
145                 150                 155                 160

Asp Phe Glu Arg Thr Leu Gly Leu Ser Ser
                165                 170

<210> SEQ ID NO 24
<211> LENGTH: 168
<212> TYPE: PRT
<213> ORGANISM: Homo sapiens

<400> SEQUENCE: 24

Asp Arg Glu Leu Pro Ser Ser Ala Thr Glu Ser Asp Gly Ser Pro Val
 1               5                  10                  15

Pro Ser Ser Gln Pro Ala Phe Pro Val Gln Ile Leu Pro Tyr Leu Tyr
            20                  25                  30

Leu Gly Cys Ala Lys Asp Ser Thr Asn Leu Asp Val Leu Gly Lys Tyr
            35                  40                  45

Gly Ile Lys Tyr Ile Leu Asn Val Thr Pro Asn Leu Pro Asn Ala Phe
 50                  55                  60

Glu His Gly Gly Glu Phe Thr Tyr Lys Gln Ile Pro Ile Ser Asp His
 65                  70                  75                  80

Trp Ser Gln Asn Leu Ser Gln Phe Phe Pro Glu Ala Ile Ser Phe Ile
                85                  90                  95

Asp Glu Ala Arg Ser Lys Lys Cys Gly Val Leu Val His Cys Leu Ala
            100                 105                 110

Gly Ile Ser Arg Ser Val Thr Val Thr Val Ala Tyr Leu Met Gln Lys
            115                 120                 125

Met Asn Leu Ser Leu Asn Asp Ala Tyr Asp Phe Val Lys Arg Lys Lys
130                 135                 140

Ser Asn Ile Ser Pro Asn Phe Asn Phe Met Gly Gln Leu Leu Asp Phe
145                 150                 155                 160

Glu Arg Thr Leu Gly Leu Ser Ser
                165

<210> SEQ ID NO 25
<211> LENGTH: 157
<212> TYPE: PRT
<213> ORGANISM: Homo sapiens

<400> SEQUENCE: 25

Gly Ala Thr Pro Pro Val Gly Leu Arg Ala Ser Phe Pro Val Gln
 1               5                  10                  15
```

Ile Leu Pro Asn Leu Tyr Leu Gly Ser Ala Arg Asp Ser Ala Asn Leu
             20                  25                  30

Glu Ser Leu Ala Lys Leu Gly Ile Arg Tyr Ile Leu Asn Val Thr Pro
         35                  40                  45

Asn Leu Pro Asn Phe Phe Glu Lys Asn Gly Asp Phe His Tyr Lys Gln
     50                  55                  60

Ile Pro Ile Ser Asp His Trp Ser Gln Asn Leu Ser Arg Phe Phe Pro
65                  70                  75                  80

Glu Ala Ile Glu Phe Ile Asp Glu Ala Leu Ser Gln Asn Cys Gly Val
                 85                  90                  95

Leu Val His Cys Leu Ala Gly Val Ser Arg Ser Val Thr Val Thr Val
            100                 105                 110

Ala Tyr Leu Met Gln Lys Leu His Leu Ser Leu Asn Asp Ala Tyr Asp
        115                 120                 125

Leu Val Lys Arg Lys Ser Asn Ile Ser Pro Asn Phe Asn Phe Met
    130                 135                 140

Gly Gln Leu Leu Asp Phe Glu Arg Ser Leu Arg Leu Glu
145                 150                 155

<210> SEQ ID NO 26
<211> LENGTH: 170
<212> TYPE: PRT
<213> ORGANISM: Homo sapiens

<400> SEQUENCE: 26

Gly Leu Cys Glu Gly Lys Pro Ala Ala Leu Leu Pro Met Ser Leu Ser
1               5                   10                  15

Gln Pro Cys Leu Pro Val Pro Ser Val Gly Leu Thr Arg Ile Leu Pro
            20                  25                  30

His Leu Tyr Leu Gly Ser Gln Lys Asp Val Leu Asn Lys Asp Leu Met
        35                  40                  45

Thr Gln Asn Gly Ile Ser Tyr Val Leu Asn Ala Ser Asn Ser Cys Pro
    50                  55                  60

Lys Pro Asp Phe Ile Cys Glu Ser Arg Phe Met Arg Val Pro Ile Asn
65                  70                  75                  80

Asp Asn Tyr Cys Glu Lys Leu Leu Pro Trp Leu Asp Lys Ser Ile Glu
                85                  90                  95

Phe Ile Asp Lys Ala Lys Leu Ser Ser Cys Gln Val Ile Val His Cys
            100                 105                 110

Leu Ala Gly Ile Ser Arg Ser Ala Thr Ile Ala Ile Ala Tyr Ile Met
        115                 120                 125

Lys Thr Met Gly Met Ser Ser Asp Asp Ala Tyr Arg Phe Val Lys Asp
    130                 135                 140

Arg Arg Pro Ser Ile Ser Pro Asn Phe Asn Phe Leu Gly Gln Leu Leu
145                 150                 155                 160

Glu Tyr Glu Arg Thr Leu Lys Leu Leu Ala
                165                 170

<210> SEQ ID NO 27
<211> LENGTH: 168
<212> TYPE: PRT
<213> ORGANISM: Homo sapiens

<400> SEQUENCE: 27

Pro Ala Gln Ala Leu Pro Pro Ala Gly Ala Glu Asn Ser Asn Ser Asp
1               5                   10                  15

```
Pro Arg Val Pro Ile Tyr Asp Gln Gly Gly Pro Val Glu Ile Leu Pro
            20                  25                  30

Tyr Leu Tyr Leu Gly Ser Cys Asn His Ser Ser Asp Leu Gln Gly Leu
        35                  40                  45

Gln Ala Cys Gly Ile Thr Ala Val Leu Asn Val Ser Ala Ser Cys Pro
    50                  55                  60

Asn His Phe Glu Gly Leu Phe His Tyr Lys Ser Ile Pro Val Glu Asp
65                  70                  75                  80

Asn Gln Met Val Glu Ile Ser Ala Trp Phe Gln Glu Ala Ile Ser Phe
                85                  90                  95

Ile Asp Ser Val Lys Asn Ser Gly Gly Arg Val Leu Val His Cys Gln
                100                 105                 110

Ala Gly Ile Ser Arg Ser Ala Thr Ile Cys Leu Ala Tyr Leu Ile Gln
            115                 120                 125

Ser His Arg Val Arg Leu Asp Glu Ala Phe Asp Phe Val Lys Gln Arg
    130                 135                 140

Arg Gly Val Ile Ser Pro Asn Phe Ser Phe Met Gly Gln Leu Leu Gln
145                 150                 155                 160

Leu Glu Thr Gln Val Leu Cys His
                165

<210> SEQ ID NO 28
<211> LENGTH: 169
<212> TYPE: PRT
<213> ORGANISM: Homo sapiens

<400> SEQUENCE: 28

Pro Leu Ser Thr Ser Val Pro Asp Ser Ala Glu Ser Gly Cys Ser Ser
1               5                   10                  15

Cys Ser Thr Pro Leu Tyr Asp Gln Gly Gly Pro Val Glu Ile Leu Pro
            20                  25                  30

Phe Leu Tyr Leu Gly Ser Ala Tyr His Ala Ser Arg Lys Asp Met Leu
        35                  40                  45

Asp Ala Leu Gly Ile Thr Ala Leu Ile Asn Val Ser Ala Asn Cys Pro
    50                  55                  60

Asn His Phe Glu Gly His Tyr Gln Tyr Lys Ser Ile Pro Val Glu Asp
65                  70                  75                  80

Asn His Lys Ala Asp Ile Ser Ser Trp Phe Asn Glu Ala Ile Asp Phe
                85                  90                  95

Ile Asp Ser Ile Lys Asn Ala Gly Gly Arg Val Phe Val His Cys Gln
                100                 105                 110

Ala Gly Ile Ser Arg Ser Ala Thr Ile Cys Leu Ala Tyr Leu Met Arg
            115                 120                 125

Thr Asn Arg Val Lys Leu Asp Glu Ala Phe Glu Phe Val Lys Gln Arg
    130                 135                 140

Arg Ser Ile Ile Ser Pro Asn Phe Ser Phe Met Gly Gln Leu Leu Gln
145                 150                 155                 160

Phe Glu Ser Gln Val Leu Ala Pro His
                165

<210> SEQ ID NO 29
<211> LENGTH: 169
<212> TYPE: PRT
<213> ORGANISM: Homo sapiens

<400> SEQUENCE: 29
```

```
Pro Val Pro Ser Ala Thr Glu Pro Leu Asp Leu Gly Cys Ser Ser
  1               5                  10                  15

Cys Gly Thr Pro Leu His Asp Gln Gly Pro Val Glu Ile Leu Pro
              20                  25                  30

Phe Leu Tyr Leu Gly Ser Ala Tyr His Ala Ala Arg Arg Asp Met Leu
              35                  40                  45

Asp Ala Leu Gly Ile Thr Ala Leu Leu Asn Val Ser Ser Asp Cys Pro
 50                  55                  60

Asn His Phe Glu Gly His Tyr Gln Tyr Lys Cys Ile Pro Val Glu Asp
 65                  70                  75                  80

Asn His Lys Ala Asp Ile Ser Ser Trp Phe Met Glu Ala Ile Glu Tyr
                 85                  90                  95

Ile Asp Ala Val Lys Asp Cys Arg Gly Arg Val Leu Val His Cys Gln
                100                 105                 110

Ala Gly Ile Ser Arg Ser Ala Thr Ile Cys Leu Ala Tyr Leu Met Met
             115                 120                 125

Lys Lys Arg Val Arg Leu Glu Glu Ala Phe Glu Phe Val Lys Gln Arg
130                 135                 140

Arg Ser Ile Ile Ser Pro Asn Phe Ser Phe Met Gly Gln Leu Leu Gln
145                 150                 155                 160

Phe Glu Ser Gln Val Leu Ala Thr Ser
                165
```

<210> SEQ ID NO 30
<211> LENGTH: 171
<212> TYPE: PRT
<213> ORGANISM: Homo sapiens

<400> SEQUENCE: 30

```
Ser Glu Arg Ala Leu Ile Ser Gln Cys Gly Lys Pro Val Val Asn Val
 1               5                  10                  15

Ser Tyr Arg Pro Ala Tyr Asp Gln Gly Gly Pro Val Glu Ile Leu Pro
              20                  25                  30

Phe Leu Tyr Leu Gly Ser Ala Tyr His Ala Ser Lys Cys Glu Phe Leu
              35                  40                  45

Ala Asn Leu His Ile Thr Ala Leu Leu Asn Val Ser Arg Arg Thr Ser
 50                  55                  60

Glu Ala Cys Met Thr His Leu His Tyr Lys Trp Ile Pro Val Glu Asp
 65                  70                  75                  80

Ser His Thr Ala Asp Ile Ser Ser His Phe Gln Glu Ala Ile Asp Phe
                 85                  90                  95

Ile Asp Cys Val Arg Glu Lys Gly Gly Lys Val Leu Val His Cys Glu
                100                 105                 110

Ala Gly Ile Ser Arg Ser Pro Thr Ile Cys Met Ala Tyr Leu Met Lys
             115                 120                 125

Thr Lys Gln Phe Arg Leu Lys Glu Ala Phe Asp Tyr Ile Lys Gln Arg
130                 135                 140

Arg Ser Met Val Ser Pro Asn Phe Gly Phe Met Gly Gln Leu Leu Gln
145                 150                 155                 160

Tyr Glu Ser Glu Ile Leu Pro Ser Thr Pro Asn
                165                 170
```

<210> SEQ ID NO 31
<211> LENGTH: 170
<212> TYPE: PRT
<213> ORGANISM: Homo sappiens

<400> SEQUENCE: 31

```
Gln Met Asn Cys Asn Leu Lys Glu Leu Lys Glu Phe Ile Asp Asn Glu
1               5                   10                  15

Met Leu Leu Ile Leu Gly Gln Met Asp Lys Pro Ser Leu Ile Phe Asp
            20                  25                  30

His Leu Tyr Leu Gly Ser Glu Trp Asn Ala Ser Asn Leu Glu Glu Leu
        35                  40                  45

Gln Gly Ser Gly Val Asp Tyr Ile Leu Asn Val Thr Arg Glu Ile Asp
    50                  55                  60

Asn Phe Phe Pro Gly Leu Phe Ala Tyr His Asn Ile Arg Val Tyr Asp
65                  70                  75                  80

Glu Glu Thr Thr Asp Leu Leu Ala His Trp Asn Glu Ala Tyr His Phe
                85                  90                  95

Ile Asn Lys Ala Lys Arg Asn His Ser Lys Cys Leu Val His Cys Lys
            100                 105                 110

Met Gly Val Ser Arg Ser Ala Ser Thr Val Ile Ala Tyr Ala Met Lys
        115                 120                 125

Glu Phe Gly Trp Pro Leu Glu Lys Ala Tyr Asn Tyr Val Lys Gln Lys
    130                 135                 140

Arg Ser Ile Thr Arg Pro Asn Ala Gly Phe Met Arg Gln Leu Ser Glu
145                 150                 155                 160

Tyr Glu Gly Ile Leu Asp Ala Ser Lys Gln
                165                 170
```

<210> SEQ ID NO 32
<211> LENGTH: 170
<212> TYPE: PRT
<213> ORGANISM: Homo sapiens

<400> SEQUENCE: 32

```
Gln Met Val Cys Asn Leu Arg Glu Phe Lys Glu Phe Ile Asp Asn Glu
1               5                   10                  15

Met Ile Val Ile Leu Gly Gln Met Asp Ser Pro Thr Gln Ile Phe Glu
            20                  25                  30

His Val Phe Leu Gly Ser Glu Trp Asn Ala Ser Asn Leu Glu Asp Leu
        35                  40                  45

Gln Asn Arg Gly Val Arg Tyr Ile Leu Asn Val Thr Arg Glu Ile Asp
    50                  55                  60

Asn Phe Phe Pro Gly Val Phe Glu Tyr His Asn Ile Arg Val Tyr Asp
65                  70                  75                  80

Glu Glu Ala Thr Asp Leu Leu Ala Tyr Trp Asn Asp Thr Tyr Lys Phe
                85                  90                  95

Ile Ser Lys Ala Lys Lys His Gly Ser Lys Cys Leu Val His Cys Lys
            100                 105                 110

Met Gly Val Ser Arg Ser Ala Ser Thr Val Ile Ala Tyr Ala Met Lys
        115                 120                 125

Glu Tyr Gly Trp Asn Leu Asp Arg Ala Tyr Asp Tyr Val Lys Glu Arg
    130                 135                 140

Arg Thr Val Thr Lys Pro Asn Pro Ser Phe Met Arg Gln Leu Glu Glu
145                 150                 155                 160

Tyr Gln Gly Ile Leu Leu Ala Ser Phe Leu
                165                 170
```

<210> SEQ ID NO 33

```
<211> LENGTH: 180
<212> TYPE: PRT
<213> ORGANISM: Homo sapiens

<400> SEQUENCE: 33

Ser Gly Ser Phe Glu Leu Ser Val Gln Asp Leu Asn Asp Leu Leu Ser
 1               5                  10                  15

Asp Gly Ser Gly Cys Tyr Ser Leu Pro Ser Gln Pro Cys Asn Glu Val
            20                  25                  30

Thr Pro Arg Ile Tyr Val Gly Asn Ala Ser Val Ala Gln Asp Ile Pro
            35                  40                  45

Lys Leu Gln Lys Leu Gly Ile Thr His Val Leu Asn Ala Ala Glu Gly
    50                  55                  60

Arg Ser Phe Met His Val Asn Thr Asn Ala Asn Phe Tyr Lys Asp Ser
65                  70                  75                  80

Gly Ile Thr Tyr Leu Gly Ile Lys Ala Asn Asp Thr Gln Glu Phe Asn
                85                  90                  95

Leu Ser Ala Tyr Phe Glu Arg Ala Ala Asp Phe Ile Asp Gln Ala Leu
                100                 105                 110

Ala Gln Lys Asn Gly Arg Val Leu Val His Cys Arg Glu Gly Tyr Ser
            115                 120                 125

Arg Ser Pro Thr Leu Val Ile Ala Tyr Leu Met Met Arg Gln Lys Met
        130                 135                 140

Asp Val Lys Ser Ala Leu Ser Ile Val Arg Gln Asn Arg Glu Ile Gly
145                 150                 155                 160

Pro Asn Asp Gly Phe Leu Ala Gln Leu Cys Gln Leu Asn Asp Arg Leu
                165                 170                 175

Ala Lys Glu Gly
            180
```